United States Patent [19]
Hepher et al.

[11] Patent Number: 5,494,813
[45] Date of Patent: Feb. 27, 1996

[54] NEMATODE CONTROL WITH PROTEINASE INHIBITORS

[75] Inventors: Andrew Hepher, Kent; Howard J. Atkinson, Leeds, both of England

[73] Assignee: Nickerson Biocem Limited, Cambridge, United Kingdom

[21] Appl. No.: 108,623

[22] PCT Filed: Mar. 5, 1992

[86] PCT No.: PCT/GB92/00390

§ 371 Date: Oct. 18, 1993

§ 102(e) Date: Oct. 18, 1993

[87] PCT Pub. No.: WO/9215690

PCT Pub. Date: Sep. 17, 1992

[30] Foreign Application Priority Data

Mar. 5, 1991 [GB] United Kingdom ................. 9104617

[51] Int. Cl.⁶ ............................. A01H 1/04; A01H 15/00; A01H 25/00; A01H 63/00; C07H 21/04; C12N 15/00
[52] U.S. Cl. ...................... 435/172.3; 47/58; 435/240.4; 435/69.1; 435/70.1; 514/2; 530/370; 536/23.2; 800/205
[58] Field of Search ............................ 435/172.1, 172.3, 435/240.4, 240.49, 69.1, 70.1, 240.5; 800/200, 205, 250, 255, DIG. 43; 935/18; 514/2; 536/23.2; 530/370; 47/58.01, 58

[56] References Cited

FOREIGN PATENT DOCUMENTS 272144  6/1988  European Pat. Off. ........ C12N 15/00

OTHER PUBLICATIONS

Ryan. 1990. Annu. Rev. Phytopathol. 28:425–449.
Miller et al. 1977. Journal of Nematology, 9(3):192–197.
Potrykus. 1991. Annu. Rev. Plant Physiol. Plant Mol. Biol. 42:205–225.
Bowles et al. 1991. Proc. Phytochem. Soc. Eur. 32:225–236.
Hilder et al. 1987. Nature. 330: 160–163.
Brunke et al. 1991. Tibtech. 9:197–200.

*Primary Examiner*—David T. Fox
*Assistant Examiner*—Erich E. Veitenheimer
*Attorney, Agent, or Firm*—Hale and Dorr

[57] ABSTRACT

The present invention is directed to methods of controlling plant parasitic nematodes using proteinase inhibitors, particularly those in the Bowman-Birk family which includes cowpea trypsin inhibitors. Nematode resistance can be conferred on plants by transforming them to express a gene or other DNA coding for a proteinase inhibitor using standard genetic engineering techniques. Alternatively, proteinase inhibitors can be provided to nematodes or to the site of their attack.

16 Claims, 5 Drawing Sheets

NEMATODE CONTROL WITH PROTEINASE INHIBITORS

FIELD OF THE INVENTION

This invention relates to the control of pests. In particular the invention relates to the protection of plants against parasitic nematodes.

BACKGROUND OF THE INVENTION

Most plant parasitic nematodes are less than 2 mm in length and develop from an egg through three or four juvenile stages (J1–J3 or J4) to adult in a life cycle lasting from a few weeks to several months. Ectoparasites and endoparasites occur and more species attack roots than aerial tissues. With very few exceptions, the nematodes use a hollow stylet both to pierce plant cell walls and to withdraw cell contents. Migration in the plant involves intracellular penetration through perforated cell walls or bodily movement between cells. Some endoparasites migrate short distances into plants before feeding whereas others move continually or rely on host growth to assist their distribution within the plant.

Several genera including both the economically important cyst and root-knot nematodes modify plant cells into feeding sites able to support sedentary females. Such individuals grow within a few weeks by up to 1000× ensuring a high fecundity.

Cyst nematodes (principally Heterodera and Globodera spp) are key pests of major crops. *Heterodera glycines* is the principal pathogen of soybean in the USA with an economic effect that may lie between US$500–1000M a year. *Heterodera shachtii* (Beet cyst nematode) is a major constraint on sugar beet growers in the EC and parts of the USA and *Heterodera avenae* (cereal cyst nematode) is a cosmopolitan pathogen of cereals with particular importance in more arid soils for instance parts of Australia. Potato cyst nematodes *Globodera rostochiens* and *G. pallida* occur in many areas of potato cropping. They are highly damaging causing an estimated £10–50M a year loss to the UK potato industry from their direct and indirect effects on production.

Root-knot nematodes (Meloidogyne spp) are associated with tropical and subtropical soils and few other pathogens out rank them in importance to world agriculture. There are many species but five are responsible for the majority of crop damage with *M. incognita* estimated to account for about 66% of all incidences of economic loss to this genus. Severity of crop losses varies but overall losses of 11–25% have been estimated for a wide range of crops in major geographical regions of the tropics.

Cultural, chemical and resistant control are the chief approaches in current use, often in an integrated manner. There is an urgent need to improve control since nematicides are among the most unacceptable compounds in widespread use. One carbamate, aldicarb and its breakdown products are highly toxic to mammals and have polluted groundwater in the USA and presumably other areas where this pesticide is widely used. Cultural control includes hidden losses that are unacceptable to specialist growers or those with few alternative, economic crops. Resistant cultivars are not always available and are often out yielded by the best susceptible cultivars so again they involve hidden losses unless nematode damage is certain to occur. The inadequacy of current crop protection testifies to the need for an effective approach to the control of nematodes.

Economic densities of cyst nematode characteristically cause stunted plants with a root system occupying a small soil volume. The diseased plants show symptoms of mineral deficiencies in their leaves and wilt readily. Yield losses are related to the severity of parasitism above a tolerance limit and can be substantially above 50% for some species. Root knot nematode causes many of the effects described for cyst nematodes with the addition that the root system is often heavily galled with increased accessibility to secondary pathogens.

A few nematodes are vectors of a narrow range of plant viruses (NEPO viruses by, Xiphinema, Longidorus, and certain TOBRA viruses by, Trichodorus). For example, Xiphinema spp. transmit the GFLV virus to vines. In addition nematodes in association with fungi are transmitted by specific insect vectors and cause a few important conditions such as pine wilt disease and red ring disease of coconut. In restricted areas of Australia a nematode introduces a Corynebacterium to the seed head of rye grass which then becomes highly toxic to grazing sheep. Disease associations with both bacteria and fungi particularly Fusarium spp contribute considerably to the economic status of Meloidogyne spp. Beneficial nodulation of legumes by Rhizobium spp can also be suppressed by soybean cyst and pea cyst nematodes.

Resistance of crops to nematodes is clearly an important goal. For nematodes, resistance is defined by the success or failure of reproduction on a genotype of a host plant species. Dominant, partially dominant and recessive modes of inheritance occur based on one to three plant genes. A gene-for-gene hypothesis has been proposed in some cases with typically a dominant R-gene for resistance being countered by a recessive V-gene for virulence in the nematode. Two examples of resistance introduced by breeders are as follows.

In relation to Globodera spp., different sources of resistance occur and allow subdivision of populations of potato cyst nematode in Europe into five forms of *G. rostochiensis* (Ro1–5) and three of *G. pallida* (Pa1–3). These pathotypes are defined as forms of one species that differ in reproductive success on deemed host plants known to express genes for resistance. The H1 gene conferring resistance to *Globodera rostochiensis* Ro1 and Ro4 is virtually qualitative and widely used commercially. Within the UK, cv Maris Piper expresses H1 and is a highly successful resistant cultivar. Unfortunately, its widespread use in Britain is correlated with an increased prevalence nationally of *G. pallida* to which it is fully susceptible.

Secondly, in relation to Meloidogyne spp., morphologically similar forms or races occur with differential abilities to reproduce on host species. The standard test plants are tobacco (cv NC95) and cotton (cv Deltapine) for the 4 races of *M. incognita* whereas the two races of *M. arenaria* are differentiated by peanut (cv Horrunner). The single, dominant gene in tobacco cv NC95 confers resistance to *M. incognita* races 1 and 3 but its cropping in the USA has increased the prevalence of other root-knot nematodes particularly *M. arenafla*. Most sources of resistance are not effective against more than one species of root-knot nematode with the notable exception of the LMi gene from *Lycopersicum peruvanium* which confers resistance to many species except *M. hapla*. Another limitation of resistance genes identified in tomato, bean and sweet potato is a temperature dependence which renders them ineffective where soil temperature exceeds 28° C.

There is clearly still a need for further and better resistance of susceptible and commercially important crops against nematodes. Novel resistance should prove of lasting value since nematodes do not have many generations per growing season and changes in importance of pathotypes arise from selection of pre-existing forms in the field rather than from mutation following introduction of the cultivar. The latter process does not occur readily for nematodes. For instance field resistance to nematicides does not occur in contrast to widespread insecticide resistance in aphids and other insects.

DESCRIPTION OF THE INVENTION

It has now been discovered that proteinase inhibitors, including trypsin inhibitors, are potent anti-nematode agents and that, therefore, delivery of a proteinase inhibitor to nematodes and/or the site of their attack could protect plants against nematodes; for example, plants transformed with a gene or other DNA coding for a trypsin inhibitor are nematode resistant.

According to a first aspect of the invention, there is provided a method of combating plant parasitic nematodes, the method comprising providing a proteinase inhibitor to nematodes, or to a locus for them. The proteinase may be provided in a manner in which the nematodes can take up the inhibitor.

According to a second aspect of the invention, there is provided the use of a proteinase inhibitor as an agent against plant parasitic nematodes.

It is preferred to use the techniques of recombinant DNA technology to enable the proteinase inhibitor to be generated at a locus for nematodes. The most convenient way of achieving this is genetically to manipulate a plant, preferably a plant which is itself susceptible to nematode attack, to express the proteinase inhibitor.

According to a third aspect of the invention, there is provided a method of conferring nematode resistance on a plant, the method comprising modifying or transforming a plant to express a proteinase inhibitor. It will be appreciated that the resistance conferred need not be complete but it will generally be conferred to a degree which is agriculturally or economically significant for the plant involved. Nematode control may usefully be limited to females, as the following illustration shows.

Details of the life cycle and pathogenicity of potato cyst nematodes are given in standard texts (Agrios, G. N. (1988) "Plant Pathology", 3rd Ed., Academic Press, San Diego, p 803 and Jones, F. G. W. and Jones M. (1974) "Pests of Field Crops", 3rd Ed., Arnold, London). The second stage juvenile J2 of the potato cyst nematode. *Globodera pallida*, migrate from the root surface intracellularly by cutting through a few plant cell walls with its stomatostylet. Once the animal reaches close to the endodermis, it selects an initial feeding cell which gradually increases in volume incorporating other cells into a syncytium which gradually takes on the character of a plant transfer cell system by about 7 days post-invasion. This animal feeds from the syncytium which is maintained throughout the feeding period of the nematode. Animals that become males feed for two stages (J2 and J3) but females also feed as pre-adults (J4) and adults. Females become of the order of 100× the body size of the males and their feeding is responsible for much of the pathology of cyst nematodes. The cultivar Maris Piper is resistant to *Globodera rostochiensis* (pathotypes Ro1 & Ro4 only) and resistance is expressed by failure of the syncytium to develop beyond the first few days of the interaction. Males develop on such plants but females are unable to develop and pathogenicity is lowered considerably. It is therefore of value to develop novel resistance that either prevents or limits development of females.

According to a fourth aspect of the invention, there is provided the use of a gene or other DNA coding for a proteinase inhibitor in the preparation of a transgenic plant having nematode resistance.

The substrate specificities of proteinases from different sources vary and do not provide a basis on which to define them. The enzymes act through four distinct catalytic mechanisms and this allows division into four classes, viz serine, cysteine, aspartic and metalloproteinases. Serine proteinases are widespread and diverse and cysteine proteinases are also widely distributed and occur in bacteria, eukaryotic micro-organisms, plants and animals. The metalloproteinases are also recorded widely but the aspartic class has a more limited distribution and seem to be restricted to eukaryotes.

A wide range of inhibitors of proteinases occur, many of which are specific for one class of proteinases. For instance, 1, 10-phenanthroline is a chelating agent acting as a general metalloproteinase inhibitor without removing the calcium that is required for activity of many enzymes including some other proteinases. Of particular interest are those proteinase inhibitors which as proteins should be substrates and not inhibitors of such enzymes. Many of these inhibitors are seed storage proteins which accumulate during development of the seed and may occur as one of the most abundant proteins in the mature seed. The currently recognized proteinase inhibitor (PI) families are: Bowman-Birk, Kunitz, potato 1, potato 2, cucurbit, the cereal superfamily, Ragi I-2, maize 22kDa and the eystatin family. Preferably the proteinase inhibitor used in the present invention is of the Bowman-Birk family; other particularly useful inhibitors belong to the maize 22kDa and cystatin families.

The cystatin family includes orzycystatin I and II, which are derived from rice. Another member of the cystatin family is derived from maize and is distinct from the maize 22kDa inhibitor. The maize 22kDa inhibitor is a bifunctional inhibitor of trypsin and α-amylase and also has anti-fungal activity.

The Bowman-Birk family includes the proteinase inhibitors isolated from *Vigna unguiculata* (cowpea). The cowpea trypsin inhibitors (CpTis) are small polypeptides of around 80 amino acids and are double-headed serine proteinase inhibitors. Protein and cDNA sequences of CpTis have been produced (EP-A-0272144, Hilder et al. (1989) "Protein and cDNA sequences of Bowman-Birk protease inhibitors from cowpea (*Vigna unguiculata* Walp.)" *Plant Molecular Biology* 13 701–710 and Hilder et al. (1987) *Nature* 300, 160–163). There are reports that variation in CpTi levels in seeds of cowpeas can be correlated with field resistance to the bruchid beetle *Callosobruchus maculatus*. Furthermore incorporation of the CpTi into artificial diets inhibits development of *Heliothis, Spodoptera, Diabroaca* and *Tribolium*. It is claimed that cowpeas can be consumed raw by humans without ill effect and that meal prepared from them does not influence the growth of rats. A cassette including a CaMV 35S promoter and the coding sequence for a mature CpTi inhibitor has been inserted into tobacco using *Agrobacterium tumefaciens*-mediated transformation. There was a correlation between level of expression of CpTi and both survival of *Heliothis virescens* and the level of damage caused by these insect larvae to the plants (Hilder et al. (1987) *Nature* 300, 160–163; EP-A-0272144).

There are many examples in crop protection of economic measures against insects being of little value against nematodes. There is no known, common correlation between natural genes for resistance against insects and nematodes. The genes for resistance against potato cyst nematode (eg H1 in Maris Piper) have never been shown to confer protection against the coleopteran, colorado beetle nor is the tomato Mi gene conferring resistance against certain forms of Meloidogyne spp. of value against insects. In addition many widely used insecticides such as organochlorines, organophosphates and synthetic pyrethroids are not effective nematicides. The exceptions include the oxime carbamate aldicarb but this has a very broad range of activity against acetylcholinesterase and is also highly toxic to mammals.

Insects show a considerable divergence in their proteinases. For instance, trypsin and chymotrypsin-like enzymes occur in locusts and the honey bee, whereas thiol proteases predominate in the digestive processes of the weevil *Callosobruchus maculatus*. Furthermore insect proteinases show a range of pH optima and inhibitors such as soybean trypsin inhibitor inhibit the proteases of some but not other insects. Therefore the effectiveness of CpTi against some insects is not even a reliable indicator of its effectiveness against others. There is no a priori reason for anticipating that nematodes have similar proteinases to insects. Nematodes are different in this respect from insects.

A correlation may be expected between food ingested and digestive enzymes. There is a large difference in mode of feeding of the biting coleopteran insect such as the seed weevil *Callosobruchus maculatus* and a phloem-feeding hemipteran such as an aphid. The latter do modify plants but they do not form syncytial cells as cyst nematodes do. When compared to the herbivory of weevils, cyst nematodes are even more distinct than aphids in their feeding mechanisms. It follows that study of insects is unlikely to provide reliable information on the feeding of nematodes.

Knowledge of nematode proteinases is too fragmentary to assume CpTi or another trypsin or even proteinase inhibitor would influence digestive processes. Much of the work on animal parasites has concentrated on enzymes secreted by infective larvae and this is correlated with invasion of host tissues and not feeding. In the case of *Ascaris suum*, the infective larvae contain serine proteinases but those of the adults assumed to have a role in digestion are thiol and carboxyl proteases. The enzymes present are stage-specific and closely related to the specific needs of animal parasitism. It is not possible to conclude that any particular proteinase inhibitor such as CpTi should influence plant parasitic nematodes from studies of the very distinct animal parasitic species.

Similarly, the free-living nematodes are microbivorous and as such the enzymes required to digest their food may be very different from those required by plant parasites. Indeed, some early work on plant parsaties suggests that they have either lower or much lower proteinase activity than free-living nematodes investigated concurrently with them.

From the above, which shows that CpTi has been described as active against insects and that nematodes are normally killed by different mechanisms, it is apparent that anti-nematode activity of proteinase inhibitors could not be predicted from the insecticidal activity of trypsin inhibitors reported in, for example, EP-A-0272144. This is perhaps particularly so when it is considered that it is stated in EP-A-0272144 at page 3, line 58 to page 4, line 2 that it is insect resistance of a transgenic plant which is increased significantly when a plant is genetically manipulated to express trypsin inhibitor throughout the plant.

Inhibitors of cysteine proteinases may be preferred for use in the invention, as evidence (presented in the Examples) that at least some of the major proteinases of nematodes are cysteine proteinases.

The preferred proteinase inhibitor useful in the invention is a trypsin inhibitor, particularly the cowpea trypsin inhibitor (CpTi), but trypsin or other proteinase inhibitors derived for example from other legumes may be advantageous in certain circumstances. The CpTi will preferably be substantially identical to natural CpTi (in one of its allelic forms), but it need not be. For example, modifications in the amino acid sequence may not impair, and may even improve, activity. Generally, it may be said that a proteinase inhibitor useful in the invention will have properties resembling a natural proteinase inhibitor and having sufficient homology to be generally accepted as a member of a proteinase family, such as the CpTi family, on normal scientific criteria. For example, nucleic acid encoding a CpTi may have sufficient homology to hybridize with nucleic acid encoding a natural CpTi under stnngent hybridization conditions. Stringent conditions are exemplified by the use of salt solution of approximately 0.9 molar at a temperature of from 35° C. to 65° C. Nucleic acid useful in the invention may additionally be such as would satisfy the above criteria but for the degeneracy of the genetic code. Glycosylation may be present or absent, as appropriate.

The Bowman-Birk type trypsin inhibitors of cowpea are encoded by a moderately repetitive family of genes which are expressed in cowpea cotyledons as four iso-inhibitors separable by ion-exchange chromatography. All four iso-inhibitors (fI, fII, fIII and fIV) have similar trypsin inhibitor activity, as measured by in vitro enzyme activation assays. The major iso-inhibitor of the cowpea is fIV. Genes encoding these iso-inhibitors have sufficient homology to cross-hybridize with full length CpTi cDNA probes in 0.45M NaCl, 0.045M Na citrate (3×SSC) at 68° C. Examples of the fIV iso-inhibitor primary sequence (determined by protein sequencing (Sammour (1985), PhD Thesis, University of Durham)) or predicted from CpTi cDNA sequencing are presented in FIG. 1 of EP-A-0272144.

The teaching of EP-A-0272144 (which is incorporated by reference to the fullest extent allowed by law) may be followed to prepare transgenie plants having nematode resistance as a result of an expressed trypsin (or other) inhibitor transgene. Briefly, the steps involved may be as follows:
1. Isolation of polyadenylated RNA;
2. Preparation of cDNA for cloning;
3. Synthesis of cDNA;
4. Second strand synthesis;
5. Treatment of ds-DNA ends for cloning;
6. Cloning into host (eg *E. coli*) using vector such as plasmid (eg pBR322 or pUC19);
7. Screening of recombinants for CpTi (or other inhibitor) coding sequence;
8. Transfer of cloned CpTi-encoding sequences to expression vector (eg Agrobacterium BIN);
9. Transfer to host vehicle for transgenesis (eg *Agrobacterium tumefaciens*); and
10. Infection of plant with host.

It will be understood that these steps do not all have to be followed slavishly. For example. DNA synthesis technology may be used chemically to synthesize inhibitor-encoding DNA. Modifications may be introduced either at the stage of de novo synthesis or by site-directed mutagenesis carried out on an existing sequence.

Equally, any suitable expression vector may be used. The choice of expression vector may be influenced by the promoter present in the vector which controls the expression of the inhibitor. Constitutive or inducible expression may be desired. Another factor is that expression may be over the whole plant or, preferably, localised; root- and other tissue-specific promoters will probably be preferred in practice. Other methods of transgenesis using an appropriate promoter-coding sequence construct may be employed; microprojectile technology may be suitable in some instances at least.

The invention may be used to combat nematodes of several genera including cyst and root-knot nematodes. Examples of cyst nematodes include the genera Heterodera and Globodera. Species within these genera include *H. glycines, H. shachtii* (beet cyst nematode), *H. avenae* (cereal cyst nematode) and potato cyst nematodes *G. rostochiensis* and *G. pallida*. Root-knot nematodes include the genus Meloidogyne, particularly the species *M. javanica, M. hapla, M. arenaria* and *M. incognita*. Other economically important nematodes include the genus Xiphinema, particularly *X. index* and *X. italiae* (which transmit the grapevine fanleaf virus (GFLV) to the vine), *X. americanum* (which is of economic importance in the USA and elsewhere) and *X. diversicaudatum* (which transmits arabis mosiac to raspberry and other plants, brome grass mosaic to cereals and strawberry ringspot to raspberry, rose, blackcurrant and other plants) and lesion nematodes such as the genus Pratylenchus, particularly *P. penetrans, P. bractrvurus* and *P. zeae* (which are associated with damage to maize), *P. coffeae, P. bractrvurus* and others (coffee), *P. coffeae* and *P. goodeyi* (bananas), *P. brachyurus* (pineapple), *P. zeae* and *P. brachyurus* (rice), *P. brachyurus* and *P. zeae* (vegetables) and *P. thornei* (wheat). It will be noted that Pratylenchus spp. have wide host ranges and are not associated with any one particular crop. *Radopholus similis* is similar to members of the genus Pratylenchus and is arguably even more important a pest for bananas.

Lesion nematodes, such as those of the genus Prarylenchus move into roots and feed through the lesions they create, attacking cells progressively as the move through the root. Periodically, the animal may leave the root and enter another elsewhere before continuing to feed and reproduce. The term "free-living" nematodes is sometimes applied to nematodes such as Xiphinema, which never enter plants but feed from the soil by piercing plant cells with their stylets. Only the stylet enters the plant; in reality these pests are ectoparasites, but the invention is nonetheless effective in combating them.

An inhibitor may be useful in providing protection against more than one economic nematode on a crop. For example, *Meloidogyne* and *Heterodera glycines* are important nematode pests for soybean, as are *Meloidogyne* and *Paratrichodorus* for maize and *Heterodera schachtii, Longidorus, Trichodorus* and *Paratrichodorus* for sugar beet.

A cyst nematode (such as Globodera or Heterodora sp.) migrates intracellularly from the root surface to the initial feeding cell forming a lesion as it penetrates. Prarylenchus behaves similarly as it migrates intracellularly. The difference is that Prarylenchus feeds from each cell before it penetrates it. If proteinases are involved in the migration process, similarities in the enzymes would be expected. Also cyst nematodes at their first feeding cell may withdraw cell contents for nutrition before modifying the cell. If so the extracorporeal digestion processes using proteinases may be similar to those of Prarylenchus. Proteins are essential to the nutrition of animals which are unable to synthesize their amino acid requirements. Proteinases are used by animals to breakdown proteins into smaller molecules (peptides) as part of the assimilation of food. Therefore nematodes feeding on plants must possess proteinases that are appropriate for digestion of the proteins present in the plant. Otherwise they would be dependent on just amino acids available in the plant cells to serve their needs. It seems inefficient for nematodes not to utilize available protein via the use of proteinases. Since many nematodes can attack the same plant (for example, potato is a host for Globodera, several Meloidogyne species and Paratrichodorus), it seems likely that they would require similar proteinases to attack the plant proteins. Therefore inhibitors should be available to inhibit protein digestion by proteinases in the manner described in invention.

A combination of different inhibitors may be used to give protection against a specific nematode or against a plurality of different nematodes. This concept is perhaps best illustrated by considering potato cyst nematode (PCN). Cysteine proteinase activity is important to both second-stage juveniles and females of PCN at both acid and near-neutral pH. It appears that metalloproteinases are of importance in second-stage juveniles at neutral pH and females at acid pH values. Therefore a combination of inhibitors of both groups would be active against the initial establishment of second-stage juveniles and also subsequent development by the female. Carboxypeptidase inhibitors from potato tubers and leaves are examples of metalloproteinase inhibitors.

Additionally, as indicated above, the invention contemplates the provision of two (or more) inhibitors to provide protection against two different nematodes which may attack the same crop but with somewhat dissimilar proteinases. For example, Meloidogyne spp. and *H. glycines* both attack soybean and Globodera spp. and Meloidogyne spp. both attack potato.

Many crops are protectable by means of the invention, and therefore candidates for being genetically manipulated to express one or more transgenie proteinase inhibitor genes. In principle, any crop or other plant which is vulnerable to nematodes, whether cyst or root-knot, may be protected by the invention. A few illustrative but non-limiting examples include vines, tobacco, tomato, cotton, oilseed rape and vegetable crops such as soybean, sugar beet, cereals and potatoes. Ornamental plants may also be protected by the invention. The invention extends to transgenic plants per se where the plants are naturally subject to attack by nematodes but not to a significant extent by insects. Preferred features of transgenic plants in accordance with the invention as for the other aspects of the invention are described above, mutatis mutandis.

THE FOLLOWING EXAMPLES ILLUSTRATE BUT DO NOT LIMIT THE INVENTION

EXAMPLES

Example 1

Preparation of transgenic potatoes

Transgenic potatoes were prepared as follows.
Construction of a CaMV-35S-CpTi gene The CpTi gene was derived from plasmid pUSSR c3/2 (Hilder, et al (1987). *Nature* 33, 160–163 and EP-A-0272144). The 240 bp CpTi coding sequence is contained within a 550 bp AluI-ScaI restriction fragment. This fragment, which also contains a longer leader sequence and a 96 bp 3' non-translated sequence, was cloned into the SmaI site of the *Agrobacterium tumefaciens* Ti plasmid vector pROK 2 (Beyan (1984). *Nucleic Acids Research* 12, 8711–8721 and Bevan et al (1985). *EMBO J.* 4, 1921–1926) giving pROK CpTi+5 (Hilder et al, 1987, supra).

The plasmid pROK 2 is a derivative of the binary *A. tumefaciens* vector pBIN 19 (Bevan, 1984 supra). It contains in addition to a kanamycin resistance gene active in plant cells, a multiple cloning site between the highly expressing constitutive CaMV 35S promoter and the nopaline synthase gene transcription termination sequence (Guilley et al (1982). *Cell* 30, 763–773 and Bevan et al (1983) *Nucleic Acids Research* 11(2) 369–385).

Figure 1:
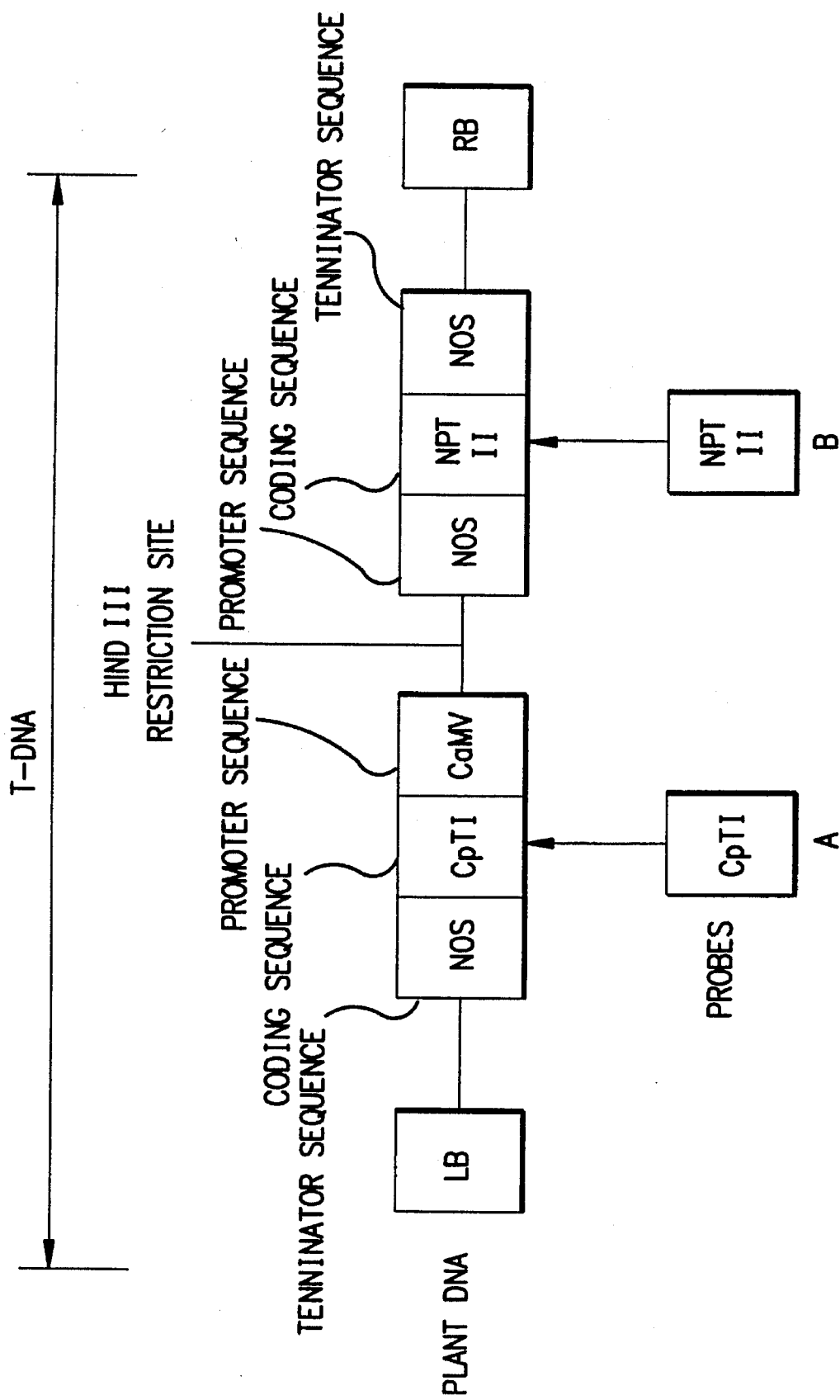
FIG. 1 shows a map of the gene structure of the T-DNA from pROK CpTi+5.

The plasmid pROK CpTi+5 was mobilised into the A. tumefaciens strain LBA 4404 containing the disarmed Ti plasmid pAL 4404 (Beyan, 1984 supra). A diagram detailing the gene structure of the T-DNA from pROK CpTi+5 is shown in FIG. 1.
Production and Regeneration of Transgenic Plants Transgenic potato shoots were produced using the Agrobacterium strain LBA4404/pAL5505 containing pROK CpTi+5 and regenerated into mature plants according to the following procedure.

Axenic shoot cultures of *Solanum tuberosum* var Desiree were maintained on standard shoot culture maintenance medium, MS salts and vitamins (Murashige and Skoog (1962) *Physiologia Plantarum*, 15, 473–497), 2% (W/V) sucrose and 0.8% (W/V) DIFCO® purified agar, pH 5.7, in a controlled environment room with a 16 h photoperiod (irradiance at 40 µE m$^{-2}$s$^{-1}$) at 24° C. (The word DIFCO is a trade mark.) Shoot apices were subcultured to fresh media every 14 days. The *Agrobacterium tumefaciens* strain containing pROK CpTi+5 was cultured in dYT medium, (16 g l$^{-1}$ tryptone, 10 g l$^{-1}$ yeast extract, 5 g l$^{-1}$ NaCl) containing 20 mg l$^{-1}$ kanamycin for 24 h at 27° C. The bacteria were then pelleted, washed three times in 2 mM MgSO$_4$ and resuspended in PCM medium (MS salts and vitamins, 2% (W/V) sucrose, 2 mg l$^{-1}$ 2,4-dichlorophenoxyacetic acid, 0.5 mg l$^{-1}$ zeatin, pH 5.7) at a density of approximately 10$^9$ cells ml$^{-1}$.

Excised squares (approximately 7×7 mm) of potato mesophyll from established shoot cultures were incubated in the bacterial suspension for 30 minutes with gentle agitation, briefly blotted and transferred, adaxial surface upwards, to PCM medium containing 0.8% DIFCO® purified agar. After 2 days culture at 24° C. (16 h photoperiod, 401 µE m$^{-2}$s$^{-1}$ PAR) explants were washed overnight in PCM containing 100 mg l$^{-1}$ augmentin, blotted and transferred to solidified PCM containing 100 mg l$^{-1}$ augmentin and 100 mg l$^{-1}$ kanamycin (acid sulphate). After 4 days culture on PCM, 100 mg l$^{-1}$ kanamycin, 100 mg l$^{-1}$ augmentin, explants were transferred to a shoot induction medium (MS salts+vitamins, 2 % (W/V) sucrose, 0.5 mg l$^{-1}$ zeatin, 2 mg l$^{-1}$ gibberellic acid, 0.8% DIFCO® purified agar, pH 5.7) containing 100 mg l$^{-1}$ augmentin and 100 mg l$^{-1}$ kanamycin. After 6 weeks culture, transgenic shoots were excised and transferred to the standard shoot culture maintenance medium for rooting. Plantlets were subcultured every 14 days until they had developed to a stage suitable for transplantation to soil (approximately 3 subcultures). Plants were then grown to maturity.
Western Blotting of SDS-Page Separated Extracts The method employed was based on that of Laemmli (1970). *Science* 227 680–685. Soluble proteins were extracted in phosphate buffered saline, (PBS, 8 g l$^{-1}$ NaCl, 0.02 g l$^{-1}$ KCL, 1.15 g l$^{-1}$ Na$_2$HPO$_4$, 0.02 g l$^{-1}$ KH$_2$PO$_4$, pH 7.2), and adjusted to a concentration of 20 mg ml$^{-1}$, 50 µl of each boiled extract was loaded onto a 17% polyacrylamide gel and electrophoresed overnight at 7 mA. The separated proteins were then transferred to nitrocellulose using a semi-dry electroblotting system (LKB Pharmacia). The free powder solution, (5 % w/v milk powder in PBS), as described by Johnson et al (1984), *Gene Analysis Techniques* 1 3–8.

Immunological detection of bound CpTi was conducted using rabbit anti-CpTi primary antibodies (supplied by Durham University), followed by $^{125}$I conjugated donkey anti-rabbit secondary antibodies (Amersham International plc, Bucks). the filter was incubated for 2 h at 42° C. with the primary antibodies and then washed for three 15 min periods with the blocking solution. After this wash, the filter was incubated with the secondary antibodies, also for 2 h at 42° C. A final filter washing followed as before, prior to drying and processing. The resultant filters were subject to conventional autoradiography. Western analysis confirmed that all transgenic clones expressed the mature CpTi protein in young leaves and roots.

Extraction of DNA and Southern Analysis

Approximately 3 g of leaf tissue was frozen in liquid nitrogen and powdered with acid-washed sand in a pestle and mortar. To the powder was then added 5 ml of 100 mm Tris-HCl (ph 8.5), 100 mM NaCl, 50 mm EDTA, 2% SDS, 0.1 mg ml$^{-1}$ proteinase K. After 1 h of gentle agitation at room temperature, 5 ml of phenol-mix (Slater (1984), The Extraction of Total RNA by the Detergent and Phenol Method in "*Methods in Molecular Biology*", Volume 2. ed. Walker, J. M., Humana Press, pp101–108) equilibrated with 100 mm Tris-HCl, pH 8.5, 100 mM NaCl, 50 mM EDTA, was added to the slurry. After 30 minutes gentle agitation the mixture was centrifuged and the aqueous phase re-extracted three times with phenol-mix: chloroform (1:1, v/v) and once with chloroform. To the subsequent aqueous phase was added 0.5 ml of 3M sodium acetate, pH 5.2, and 10 ml of 100% ethanol at room temperature. The precipitated DNA was spooled out using a sterile plastic loop and resuspended in 0.4 ml TIE buffer containing 50 μg $^{-1}$RNAse for 1–2 h at 37° C.

The DNA was then re-extracted as before and precipitated from the aqueous phase by adding 0.1 volume of 3 m sodium acetate, pH 5.2, and 2 volume of 100% ethanol, and incubating overnight at −20° C. The DNA was then washed (×2) in 70% ethanol, resuspended in 50 μl double-distilled, sterile water and stored at −80° C. 10 μl samples were digested with the restriction enzyme HindIII and electrophoresed overnight on a 0.8 % agarose gel at 25 V. Standard techniques, as described by Maniatis et al (1982) Molecular Cloning: *A Laboratory Manual*, Cold Spring Harbor Laboratory, were used.

The gel was then depurinated in 0.25M HCl for 10 min at room temperature, rinsed in distilled water and denatured in 1.5M NaCl, 0.5M NaOH for 20 min at room temperature. The DNA was transferred to a nylon membrane (GENE SCREEN PLUS®, DuPont Co, NEN Products, Boston, Mass., USA) using an LKB VACUGENE® Vacuum Blotting System (Pharmacia Ltd, Milton Keynes, Bucks, UK). (The expressions GENE SCREEN PLUS® and VACU-GENE are trade marks.) Transfer was for 60 min at room temperature under 40 cm H$_2$O vacuum in 0.4M NaOH. following transfer, the filter was neutralised in 1.5M NaCl, 0.5M Tris, pH 7.5 for 15 min at room temperature and thoroughly air-dried. Filters were stored at 4° C. prior to hybridization.

Filters prepared in this way were treated with one of two probes (FIG. 1). These were the 564 bp AluI/ScaI fragment from pUSSR c3/2, which contains me CpTi coding sequence, and the 800 bp PstI/BamHI fragment from pNEO which contains the coding sequence for the NPT II kanamycin resistance gene. (pNEO is a pUC8 derivative containing the chimeric kanamycin resistance gene found in pBIN6 (Bevan, 1984, supra) and was obtained from the Department of Biological Science, Durham University.) Both probes were labelled to a high specific activity (>9×10$^8$ dpm μg$^{-1}$) using a random priming kit (Boehfinger Manrheim Ltd, Sussex). Standard techniques for hybridization and washes were used (Maniatis et al, 1982 supra). Filters were autoradiographed for 4 d at −70° C.

FIG. 1 shows the structure of the T-DNA containing the chimeric CpTi gene which was introduced into the potato plants. A unique HindIII restriction site is present between the CpTi and NFT II genes. Thus, a HindIII digest of a plant genome containing a single copy of the T-DNA will generate two junction fragments. As the site of integration, and hence the distance to the next adjacent HindIII recognition sequence in the plant DNA, will vary between individual transformants, the size of the junction fragments will also differ. Similarly, multiple copies of the T-DNA integrated at different sites within the same genome will produce a commensurate number of bands when probed with a sequence specific to one of the junctions. This enables gene copy number to be determined unambiguously.

For Southern analysis, genomic DNA was extracted from one line that was expressing CpTi relatively highly and two low-expressing lines and restricted with HindIII. After separation by gel electrophoresis, and subsequent blotting, the resulting falters were probed with either the CpTi or kanamycin resistance coding sequences.

The two low expressing lines each gave a single band, denoting the presence of a single copy of the chimeric CpTi gene integrated into the plant DNA. As expected the bands were of different sizes, indicating that integration had occurred at a different site within the genome of the two transformants. The relatively high-expressing line has approximately seven copies of the CpTi gene.

Strong hybridization to a probe derived from the NPT II coding sequence was observed in genomic DNA extracted from all three CpTi positive lines.

Alternatively, transgenic potatoes can be made by methods analogous to those described in EP-A-0272144.

Example 2

Establishment and Development of *G. pallida* in transgenic potatoes—Culture of transgenic plants Transgenic potatoes prepared as described above were initially handled as ex-plants grown monaxenically on 50 ml of nutrient agar in 250 ml screw top glass vessels. These plants were grown in a plant growth chamber (Conviron S10H) on a day night-cycle of 16 h light and 8 hours dark at 20° C. and a photon flux intensity of 80 $\mu E/m^2$. They were sub-cultured every 14 days by taking lateral stems and establishing new plants in further sterile pots. Four plant lines were cultured in this way. One had previously been shown to express a high level of cowpea trypsin inhibitor (CpTi) and the second was transformed with a similar construct which lacked the CpTi gene. A third plant clone expressed the pea lectin and the final clone was again a similar construct but lacking the pea lectin.

In the first experiment, pea lectin plants and their controls were transferred from the agar culture to small pots with a diameter of 5 cm containing sand with grains of 50–400 µm to favour nematode invasion. A total of 500 freshly hatched *Globodera pallida* were added to each pot. After four days, the sand plus the nematodes that had failed to invade were washed from the plant which was re-planted in a sandy loam soil. The number of animals on the plant was assessed at 4 days and 21 days post-invasion.

In all subsequent experiments, batches of explants were transferred to growth pouches (Northrup-King, Minneapolis and Vaughan Seed Co., Ill.) rather than sand or soil. They were grown in the pouches containing 10 mls of 25 % strength Hoaglands salt medium and grown for a further 10 days in the conditions already given. They were then ready for infection with *Globodera pallida.*

A population of *Globodera pallida* that is the reference population for the pathotype Pa2 was cultured on cv Maris Piper in pots out-doors and the infected soil dried and stored. When required for these experiments cysts were extracted by flotation from the dry soil (Southey, J. F. (1986), "Laboratory Methods for Work with Plant and Soil Nematodes", Her Majesty's Stationery Office, London). The cysts were separated from other floating debris by rolling down a metal, inclined plane. Cysts in batches of several hundred were soaked in tap water for 7 days at 15° C. before transfer to a 40 μm nylon mesh which was part submerged in potato root diffusate. This solution was collected in the standard manner (Southey, supra)) by passing water through the root ball of a young potato plant and storing the leachate in plastic bottles at 4° C. The diffusate was filtered before use.

Juveniles emerged from the cysts and were used within 2 days of emergence. Experiments were timed so that sufficient juveniles were available on one day to infect a series of experimental and the corresponding control plants.

Plants were infected 1 cm behind 4–6 root tips per plant after the roots had grown down the paper of the pouch onto a band of glass fibre filter (Whatman 1 A). 50 J2 were introduced in about 10 μl potato root diffusate tap water to the surface of the root at 1–2 cm from the tip and a second piece of glass fibre placed over the root. The filters were removed after a further 24 hours and the root systems washed with water to remove nematodes that had failed to enter the roots by that time. Plants were returned to the growth chamber in their pouches until harvested at the completion of the experiment.

Infected roots were removed from the plant and immediately plunged into boiling 1% acid fuschin (44) for 1 minute. The roots were destained for about 24 h in acidified glycerol at 50° C. leaving the stained nematodes clearly visible in the roots. The number of nematodes in each root tip and their developmental stage and position relative to the vascular tissue were recorded. In some experiments, the volume of each nematode was estimated in the following way. The outline of the individual was drawn using a 40× objective and a camera lucida onto an acetate sheet. A micometer scale was also transcribed in a similar way. The sheet was then attached to the screen of an MS-DOS microcomputer (AMSTRAD 1512) and the outline of an individual was copied using a computer mouse. The expressions MS-DOS and AMSTRAD are trade marks.) A computer program written for the work was used to estimate volume from the outline of the nematode.

Results & Discussion

Plants infected m sand gave similar infection rates at 4 days post-infection for the clone expressing pea lectin and its control. After 21 days, most males have left the plant but the percentage of animals added to the sand that had established and become females was similar for both clones (Table 1).

TABLE 1

Percentage of G. pallida establishing and maturing on transgenic potatoes grown in sand and soil

| Gene expressed | Establishment (4 days) | Females (21 days) |
|---|---|---|
| Control | 21.8 ± 2.5 | 13.3 ± 1.6 |
| With Pea Lectin | 21.9 ± 2.4 | 14.8 ± 1.8 |

Plants were transferred from sand to soil at 4 days.
Values are means ± SEM; 100% = 500 nematodes/plant.

Plants infected in pouches were typically infected with 20–30% of the animals added to the root surface with an invasion period of just 24 hours. This restricted period for infection gave similar percentage invasions to those achieved over 4 days for the experiments with plants in sand and had the advantage of providing highly synchronous infections. No animals entered the root before 15 hours giving a band of about 9 hours between the first and last individual allowed to invade. This was an adequate degree of synchrony for these experiments.

Expression of pea lectin in the potato roots did not prevent establishment of the nematodes at 2, 4 or 8 days after invasion (Table 2).

TABLE 2

Establishment of G. pallida at a feeding site in transgenic potatoes

| Gene expressed | % established at three times post infection | | |
|---|---|---|---|
| | 2 days | 4 days | 8 days |
| Control | 29.3 ± 4.5 | 25.5 ± 4.1 | 27.1 ± 3.2 |
| With Pea Lectin | 32.2 ± 4.8 | 25.9 ± 4.5 | 26.2 ± 3.5 |
| Control | 21.0 ± 3.0 | 20.7 ± 3.2 | 23.5 ± 3.4 |
| With CpTi | 18.0 ± 3.2 | 19.4 ± 3.6 | 17.7 ± 4.1 |

Values are mean percentage of nematodes/root tip ± SEM
(100% = 50 nematodes/root tip).

There was a slightly lower invasion rate for CpTi plants than their corresponding control but this effect was not statistically significant.

Figure 2:
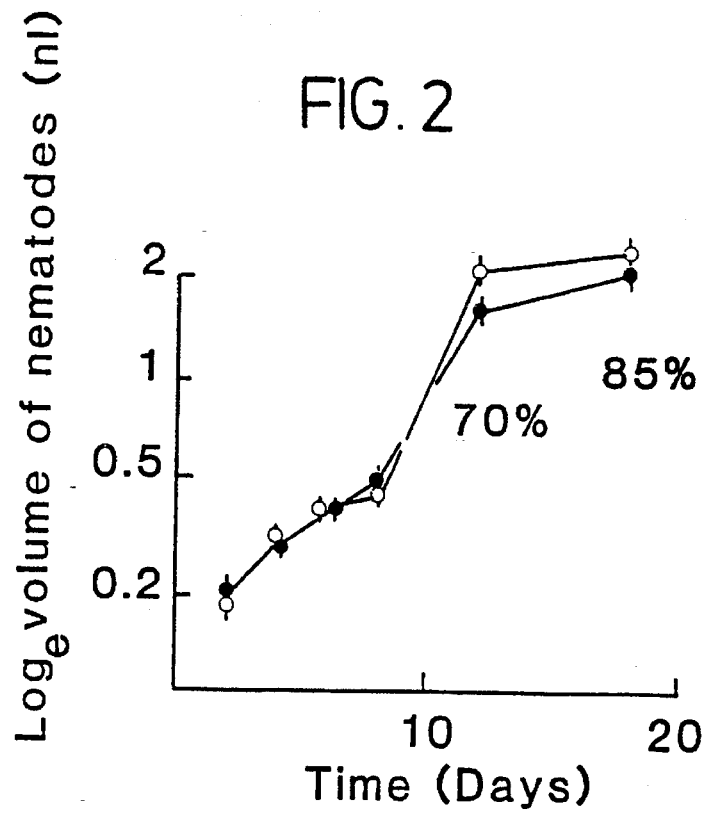
FIG. 2 shows the growth of *Globodera pallida* on transgenic potato plants measured as changes in body volume with time after introduction of infective juveniles to roots of the plant. Plants either expressed (solid circles) or did not express (open circles) pea lectin gene. The volume of the nematodes from plants expressing pea lectin was 70% and 85 % of the controls at 12 and 16 days respectively. The values for volume are given as natural logarithms and they show an exponential daily increase of 23.9%/day over 2–12 days for those nematodes on the control plants.
Figure 3:
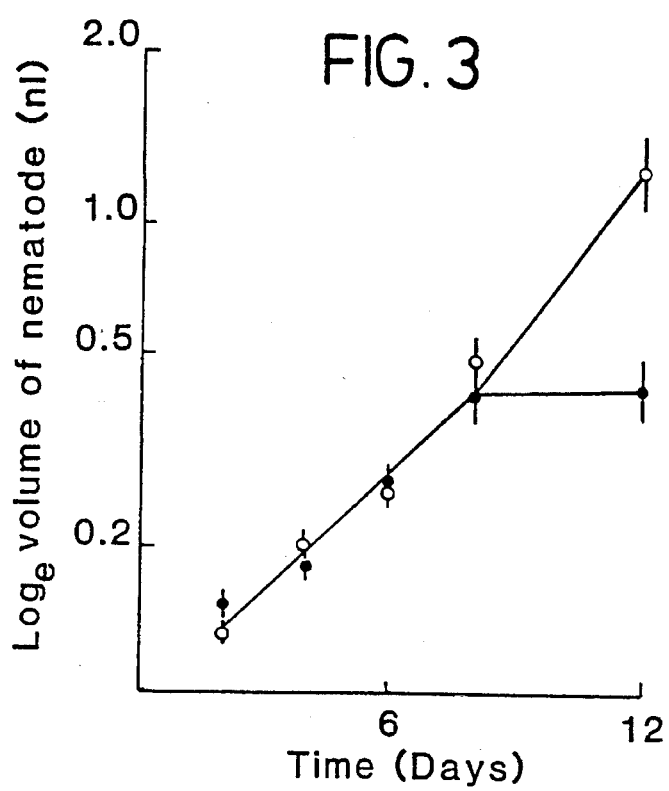
FIG. 3 shows the growth of *Globodera pallida* on transgenic potato plants measured as changes in body volume with time after introduction of infective juveniles to roots of the plant. Plants either expressed (solid circles) or did not express (open circles) cowpea trypsin inhibitor (CpTi). The volume of the nematodes from plants expressing CpTi was significantly less than for the controls after 12 days. The body volume is given as natural logarithms and they show an exponential daily increase of 21.3%/day over 2–12 days for those nematodes on the control plants.

The growth of Globodera pallida after invasion followed a logistic curve which approximates to an exponential curve in the early stages of infection (FIGS. 1 & 2). On invasion, the animals have an estimated volume of 126±1.9 pl. In the case of the experiments with pea lectin, the volume increased by 23.9 % over the first 12 days. The volume of the animals on the pea lectin plants was 70% of that for the controls at 12 days and 85% at 16 days. Clearly the exponential phase of growth was not maintained beyond 12 days and so the subsequent experiments with CpTi plants were terminated at 12 days. The growth rates for the nematodes in these experiments on control plants was equivalent to 21.3% increase in volume/day for 0–12 days. The growth rate was similar for 0–8 days for the plant expressing CpTi but the animal did not increase significantly in volume between 8 days and 12 days (FIG. 3).

Suppression of growth rates could affect both sexes or could occur because female development is prevented. The latter effect occurs for Globodera rostochiensis Ro1 on cultivars carrying the H1 gene which confer resistance to this pathotype of that species. Therefore each animal on the CpTi plants and the corresponding control plants were allocated to a developmental stage. The invasive stage (J2) and the subsequent stage are both small and were considered together for this analysis. The sex of the pre-adult stage can be discriminated readily and were sexed accordingly. Adults had not developed by day 12.

Figure 4:
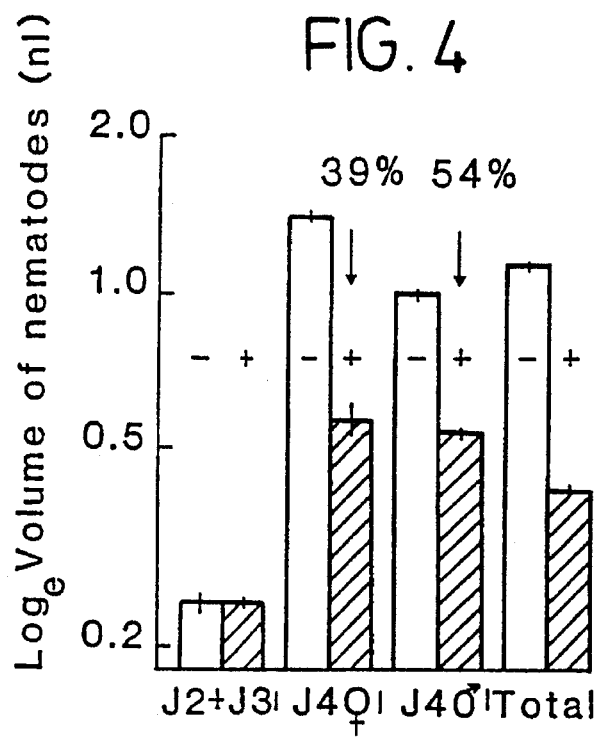
FIG. 4 shows the body volume of developmental stages of *Globodera pallida* present on potato plants 12 days after introduction of infective juveniles to the roots. Plants either expressed (+) or did not express (−) cowpea trypsin inhibitor (CpTi). The body volume is given as natural logarithms and the sex of the immature animals determined for the pre-adult (J4) stage. The volume of immature adults and females on the CpTi plants was 39 % and 54 % for females and males respectively.

The results establish that pre-adults of both sexes were smaller than on the control plants at day 12 (FIG. 4). The pre-adult male is undergoing development within the cuticle of the third stage and the overall size of these animals was only 39% of the controls. In the case of females, the pre-adults on CpTi plants were only 54% of the size of those on the control plants.

Figure 5:
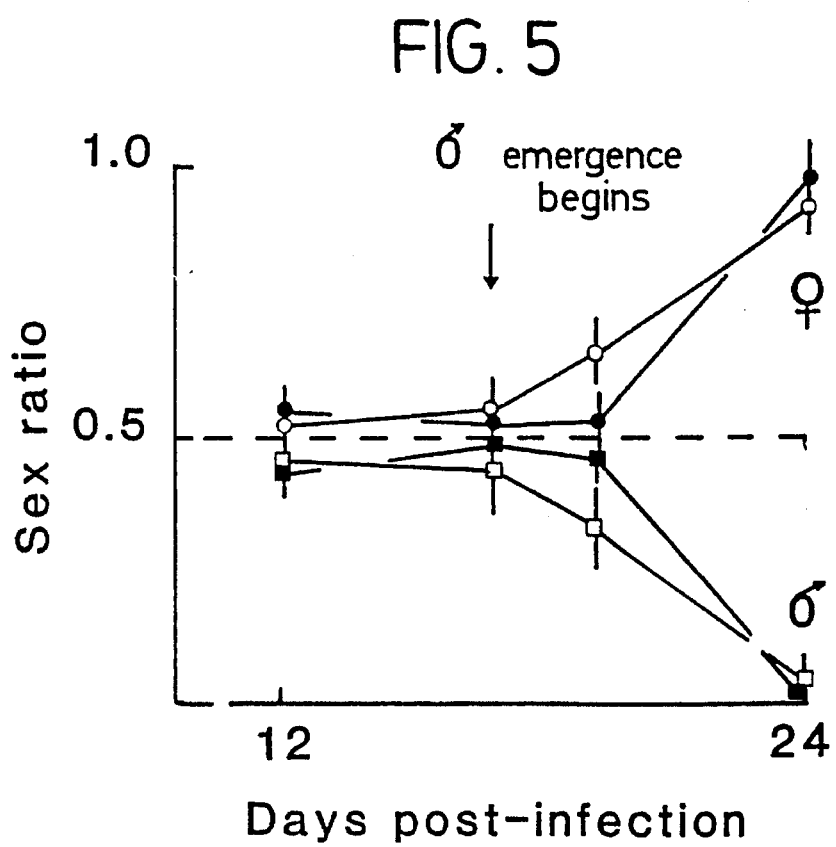
FIG. 5 shows the proportion of each sex of *Globodera pallida* on transgenic potato plants 12–24 days after introduction of infective juveniles to roots of the plant. Plants either expressed (solid symbol) or did not express (open circle) pea lectin gene; (males are represented by squares and females by circles).

The development of males and females was followed more completely for the pea lectin experiment. Sex ratios were determined at 12, 16, 18 and 24 days post-addition to the roots. The sex ratio remained at about 1 male: 1 female to beyond 16 days (FIG. 5). Beyond that time males emerge from the juvenile cuticle that encloses them and migrate from the root in search of females. This leads to a shift in the sex ratio in favour of females which remain associated with roots for many more weeks. Plants expressing pea lectin showed a small but significant delay in this shift with a significant difference in the ratios at 18 days. This is consistent with the slight drop in growth rate of the animals which may result in a small delay in reaching the adult male stage.

Figure 6A:
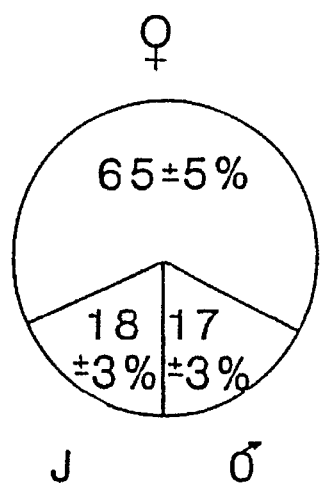
FIG. 6 shows pie charts giving the percentage of each sex of *Globodera pallida* on transgenic potato plants 12 days after introduction to roots of the plant. Plants either expressed (right chart) or did not express (left chart) cowpea trypsin inhibitor. Results are based on observation of over 120 nematodes for each treatment. Animals that were too immature to sex are included (J).
Figure 6B:
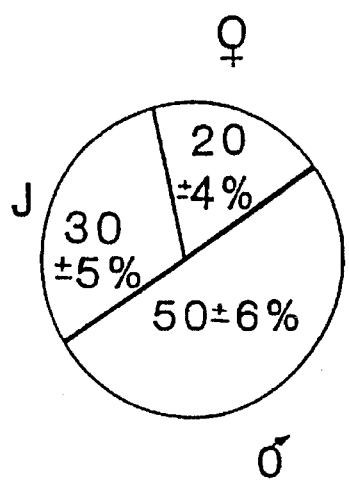

Experiments with CpTi plants were completed at 12 days since the low growth rates at this time may have resulted in differential death of one sex which would distort the sex ratio data. At 12 days, the majority of animals could be sexed accurately but there were some for which this could not be achieved and they were recorded in the results as juveniles. Both sexes feed as third stage juveniles but males do not feed from the plant as either pre-adult or adults. Females feed extensively for more than a further 25 days and it is this phase that is responsible for most of the pathological effect on the plant. Over 120 animals were examined for both CpTi and control plants. In the case of the controls 65±5% were female, 17±3% male and 18±3% juveniles (FIG. 6). This is a very similar percentage of females developing from animals establishing to that obtained in earlier experiments in which pea lectin and control plants were used (Table 1). In contrast, the percentage of females on CpTi plants was 30%, males 50±6% and juveniles 30±5% (FIG. 6). The large fall in numbers of females compared to the controls was statistically significant ($X2<0.005$). One possibility is that this is due to a reduction in development influencing the proportion of females relative to males recognized at 12 days. Even if all unsexed individuals at 12 days are indeed females, the modified sex ratio of 50:50 females to males gives significantly less frequent occurrence of females than for the controls. It is necessary to make the double, unreasonable assumption that female development is slowed on CpTi plants but the development of males is increased on these plants to eliminate statistical significance. If this unreasonable double assumption is made then the ratio for CpTi is 50:50 and for the controls 65 female: 35 males. It seems particularly unreasonable to assume that the CpTi plants which cause males to have a volume of 54% of the controls should also speed their development to adulthood. Another possibility if sex is irreversible for this species is that fewer female juveniles enter the CpTi plants rather than the controls. A more interesting possibility is that environmental sex determination occurs resulting in relative reduction in the number of animals able to develop to female on the CpTi plants.

The results establish two effects of CpTi plants on *Globodera pallida*. The growth rate of the animal is reduced and the likelihood of the animal becoming female is reduced. The reduction in growth rate may reduce the final size of the female or increase the time taken for full size to be attained. In both cases the overall reproduction of the animal on the crop will be reduced either by lowering the overall size and egg production of the female or by extending the life cycle and reducing the opportunity for subsequent generations to develop on the crop. The overall effect of reducing the number of females on the plant and either the fecundity or increasing the prepatent period is substantial. For instance the reduction of the incidence of females in this work from a ratio of 0.65 of the total to 0.2 of the total is an overall reduction in frequency of 70%. If females fail to grow beyond 12 days they would be too small to contain more than 10 eggs which is about 5–10% of their normal size. Assuming that the effect on the proportion of females is slight but the actual egg production is reduced by 75%, then the overall result of both effects in tandem can be calculated as $(1-0.75)\times(1-0.65)=0.0875$. This is equivalent to a reduction in reproduction of more than 90%.

Pest management of cyst nematodes can be achieved by a single control procedure or by integrated control. Economic thresholds for PCN vary according to agronomic conditions but 10 viable eggs/g soil at planting is a typical value. The objective of control is to ensure that sufficient individuals are killed prior to reproduction or egg population declines sufficiently post-harvest to ensure the population is again at this level when the crop is planted on the next occasion. Multiplication is density dependent and is also influenced by the environmental conditions during cropping but a typical value of a population at the economic threshold at planting is 10×. Therefore one control measure action alone must impose at least 90% mortality to achieve full economic control. Measures less effective than about 90% must be used in combination with other control measures. The cv Maris Piper is capable of imposing a 90% mortality on *Globodera rostochiensis* but other cultivars showing resistance against *G. pallida* often do not achieve this level of suppression of reproduction. The results with the CpTi plants are very encouraging. It seems that the combination of reducing growth rates, female size and fecundity plus a shift in sex ratio towards males may combine to achieve an overall mortality in excess of 90%.

Example 3

Evidence that Major Proteinases of Nematodes Include Cysteine Proteinases

Little is known of the roles for proteinases in the invasion, establishment and feeding processes of cyst nematodes although this has been defined to some extent for the very distinct requirements of animal parasitic forms. Extracorporeal secretion of proteinases may occur during migration, syncytial induction and subsequent feeding and thus these enzymes are likely to have a major intracorporeal role in digestion. The severe effect of CpTi plants on *G. pallida* is likely to be a direct effect upon such proteinases of the nematode rather than acting indirectly on plant proteinases in the syncytium or elsewhere. Therefore experiments to study proteinase activity in females of *G. pallida* have been conducted to confirm the presence of such enzymes in feeding individuals.

(1) pH Dependence of the Proteolytic Activity of *G. pallida*

Females of *G. pallida* were removed from potato roots and homogenised in EDTA (1 mm)-NaOH buffered distilled water (pH 6.0). The nematode homogenate was clarified by centrifugation at 13,000 g for 2 min and passed through non-absorbent cotton wool. The filtrate was used directly as the source of crude proteinases. pH was controlled using 0.1M of citrate-phosphate, sodium-phosphate and phosphate-carbonate buffers for pH 3.0–6.0, pH 6.5–7.5 and 8.0–8.5 respectively. These buffers were mixed with equal volume of the nematode homogenate and RUBISCO (150 µg) in 0.04% SDS resulting in a final reaction volume of 75 µl. The mixture was incubated at 25° C. for 60 min and enzyme activity terminated by adding 25 µl of 15% (w/v) TCA. The tubes were kept on ice for 30 min for full precipitation to occur. The supernatant was clarified by centrifugation (13,000 g, 2 min). The liberation of TCA-soluble amino groups from digested RUBISCO was used to quantify the proteolytic activity of nematode homogenates using 2, 4,6-trinitrobenzsulphonic acid (TNBS). TNBS reagent was made by mixing one volume of 0.3% (w/v) TNBS in water with four volume of 4% (w/v) sodium tetraborate in 0.15M NaOH. 250 μl of the reagent was mixed with 75 μl of sample and the reaction was allowed to proceed for 60 min at 30° C. before terminating by adding 1.25 μl of 0.5M HCl. The absorbance at 340 nM was read against both homogenate and RUBISCO controls. Results are expressed as nmol of TCA-soluble amino groups liberated per min at 25° C. using a standard curve based on L-leucine in CP buffer.

Subsequent work was based on pH 5.7 using CP buffer. Females of *G. pallida* were rinsed in 50 mM CP buffer plus 1 mM EDTA and homogenised in ice-cold 50 mM CP buffer, centrifuging and filtering as before. The EDTA wash step was omitted for experiments using inhibitors or activators (see below).

(2) Proteinase Assay for Inhibitor or Activator Studies

25 μl of RUBISCO (from a stock solution in CP buffer of 1 mg/ml containing 0.04% SDS) was added to 20 μl of the sample homogenate and either 5 μl CP buffer or 5 μl of inhibitor/activator. After incubation for 60 min, the reaction was stopped by adding 30 μl of denaturing buffer and boiling for 2.5 min.

(3) Inhibitors and Activators

Stock inhibitor and activator solutions (Table 3) were made up in buffer and added to the nematode extract. The inhibitor/activator was pre-incubated with the enzyme solutions for 30 min at 25° C. before addition to the protein substrate (4) Electrophoresis The SDS-denatured mixture was subjected to SDS-PAGE using a 12.5% resolving gel and a current of 30 mA for about 4 h. The gel was stained using Coomassie Brilliant Blue.

(5) Studies with Gelatin

Females of *G. pallida* were homogenized in CP buffer as before, spun at 13,000 g for 2 min and passed through non-absorbent cotton wool. The clear filtrate was used with 0.6M sucrose and 0.001% bromophenol blue for non-denaturing (native) polyacrylamide electrophoresis (NPAGE).

(a) Gelatin Electrophoresis

9% polyacrylamide gels containing 0.1% gelatin were prepared by dissolving the gelatin in a resolving gel mixture at c. 50° C. The nematode samples were loaded onto a gelatin-free 2.5% stacking gel and electrophoresis conducted at 30 mA with tap-water cooling for about 4 h. The high molecular weight gelatin substrate (but not the proteins of interest) was rendered immobile in the 9% polyacrylamide gel.

Gels were rinsed briefly in distilled water, placed in 75 mM CP buffer containing 0.02% SDS and incubated overnight at 25° C. Proteolytic activity was visualized as zones of reduced coloration following staining with Coomassie Blue. In a second experiment, samples were run in 9% gels without gelatin. Two series of 10×1 cm slices were cut from the 10 cm gel. One series was denatured immediately by boiling for 2.5 min with sample buffer, and the second incubated overnight with RUBISCO (25° C.) before denaturing. The non-RUBISCO-treated segments were run on SDS-PAGE (12.5% resolving gel for 4 h, fixed in methanol, acetic acid water (40:10:50; v/v) and the resultant fractionated proteins visualized by silver staining. Segments incubated with RUBISCO were boiled in sample buffer and the samples run on an 12.5% SDS-PAGE system. The gel was stained with Coomassie Blue.

(b) Gelatin-Affinity Chromatography

Gelatin-binding proteinases were extracted with gelatin-agarose (Sigma). Clarified female homogenate (0.5 ml) was loaded on a 0.75 ml bed volume gelatine-agarose (12.0×0.8 mm) which was previously equilibrated with CP-DTT. The column was washed with CP-DTT, and the final buffer-DTT elution was collected (0.5 ml). Then, eluting buffer (containing 0.2M glycine, 0.25M cysteine and 0.5M NaCl) was loaded, and six 0.5 ml fractions collected. Finally, CP-DTT was passed through the column and three 0.5 ml fractions collected. Individual fractions were dialyzed against 25 mM CP buffer at 4 C. to remove NaCl and amino acids. Aliquots were taken for either incubation with RUBISCO and subsequent SDS-PAGE analysis, or denatured immediately. Samples treated with RUBISCO were incubated overnight at 25° C. and the reaction terminated by boiling with sample buffer for 2.5 min.

(6) The Use of a Mercuryl Column to Isolate *G. pallida* Proteinares

The apparent cysteine proteinases of *G. pallida* should possess active thiol groups that may allow their recovery with organomercuryl reagents such as p-aminomercuribenzoate (PAMBA) which is a potent inhibitor of *G. pallida* proteinases (Table 3). A settled volume of 0.75 ml of p-hydroxyl(amino)-mercuribenzoate-agarose (Sigma) was poured into a 2 ml plastic syringe and washed with six column volume of 50 mM sodium phosphate buffer (pH 8.0). The agarose column was then prepared with 2.5 mM mereaptoethanol, 15 mM sodium sulphite in sodium phosphate buffer (pH 8.0). This thiol reagent maximizes thiol protein binding, and favors a reversible interaction between the protein and the inhibitor. The column was further washed with five column volume of 50 mM PC buffer (pH 5.7).

Immature females were homogenized in PC buffer (pH 5.7) containing 10% (v/v) dimethyl sulphoxide, 0.5% (v/v) butanol, 0.1M KCl, 1 mM EDTA and 10 mM sodium sulphite. 0.5 ml of the homogenate was added to the column and this volume of elutant recycled onto the column 3× before the final elutant of 0.5 ml was kept (fraction 1).

The column was washed free of unbound thiol proteins with 5×0.5 ml volumes of PC buffer (pH 5.7) and all the fractions were collected. The proteins of interest were liberated from the column with either 2 mM $HgCl_2$ or 10 mM mercaptoethanol in CP buffer (pH 5.7). Again, 5×0.5 ml portions were collected and the column was finally washed with 3×0.5 ml CP buffer. Each fraction was concentrated by dialysis against 20% (w/v) polyethylene glycol (MW 3,500) and the $HgCl_2$ fractions treated with denaturing buffer and prepared for SDS-PAGE. Fractions collected from the mercaptoethanol elution were dialyzed extensively against CP buffer (pH 5.7) at 4° C. to remove the mercaptoethanol and concentrated by dialysis against polyethylene glycol as before. Samples were divided into two, and the first aliquot added to 0.6M sucrose, 0.001% bromophenol blue and loaded onto a 9% gelatin-NPAG and run with a tris-veronal buffer system (pH 8.0). The gels were soaked for 5 h in PC buffer (pH 5.7) plus 0.02% SDS. The gel was stained with Coomassie Blue and destained according to the standard procedures.

The second aliquot was incubated overnight with RUBISCO, and the reaction stopped by boiling in denaturing buffer for 2.5 min. The samples were run on a SDS-PAGE system and the gel was stained with Coomassie Blue.

pH Dependence of Proteolytic Activity of *G. pallida*

The influence of pH on hydrolysis of RUBISCO by the homogenate of developing females is shown for pH 3.0–8.5 and pH 5.0–6.5. The pH optimum for RUBISCO-digesting proteinases was 5.7 with a possible second peak at 7.5. This could indicate either (i) two groups of proteinases expressing maximum activity at their respective optimum pH; or (ii) a single major proteinase manifesting itself in both acidic and alkaline conditions. The former may be the case as a spread of activity between pH 5.0–6.5 was observed. This suggests the presence of more than one acid proteinase. A sudden drop in enzymatic activity at neutral pH and then a rise at pH 7.5 implied an alkaline-dependent proteinase.

A more detailed study was directed toward the acid proteinases which revealed maximum proteolytic activity at pH 5.7. Furthermore, a consistently high activity through the acidic pH range of 5.4–6.5 does not discount the possible presence of more than one proteinase in crude extracts of female nematodes.

Phosphate was included in all buffers so as to give a negative feedback inhibition of protein kinases, safeguarding the proteinases against phosphorylation which could render them inactive.

Effect of Activators and Inhibitors

In order to elucidate the effect of activators and inhibitors on the proteolytic activity of nematode proteinase(s), RUBISCO was treated with the extract at 25 C. at a substrate protein-nematode protein ratio (w/w) of 8. After a 30 min incubation, the reaction mixture was terminated and analysed by SDS-PAGE. The RUBISCO substrate band in the gel was quantified densitometrically (Joyce Loble Chromscan 3), and the amount of protein remaining gave an estimation of the rate of activity of the proteinase.

The presence of the sulphhydryl reagents DTT and cysteine stimulated endoproteinase activity (Table 3). In contrast, almost total inhibition of proteinase was evident when the extract was incubated with all three mercuryl compounds (PAMBA, PMA and PAMSA). There was a small but slight inhibition of proteolytic activity by the cysteine inhibitor E-64 (21%; Table 3). [E-64 (L-trans-epoxysuccinyl-leucylamide-(4-guanidino)-butane) is a potent, irreversible inhibitor of cysteine proteinases which does not affect cysteine residues in other enzymes and which does not react with low molecular weight thiols such as 2 mercaptoethanol.] This suggests that the major proteinase(s) responsible for the degradation of RUBISCO at pH 5.7 is (are) cysteine in nature. Confirmation was obtained by an increase in activity when the enzyme(s) were incubated with DTT and cysteine. It is uncertain if these reducing agents increased directly the activity of the proteinases, or increased the susceptibility of the substrate to enzymatic cleavage.

TABLE 3

Influence of inhibitors on the endoproteinase activity of G. pallida.

| Inhibitor | target proteinase | % enzyme activity |
|---|---|---|
| Control | — | 100 ± 7 |
| E-64 | Cysteine | 79 ± 6* |
| PAMSA | Cysteine | 7 ± 5*** |
| PAMBA | Cysteine/serine | 3 ± 4*** |
| PMA | Cysteine/serine | 11 ± 6*** |
| DTT (activator) | Cysteine | 128 ± 11* |
| Cys (activator) | Cysteine | 112 ± 5* |

Values are means _ SEM and differ from control; *P < 0.05; ***P < 0.001

Proteolytic Activity in Gelatin-Polyacrylamide Gels

The proteolytic activity in the upper regions of the gel suggests relatively high molecular weight proteinases. There are two or three zones of hydrolysis that are represented by Rf values of 0.28, 0.33 and 0.38. This may indicate distinct enzymes or isoforms of one enzyme. Segments of gel run in parallel but lacking gelatin, only revealed one major polypeptide with a Mr of about 62K. Moreover, incubation of the regions expressing gelatin degradation with RUBISCO resulted in the hydrolysis of the substrate protein. A further region of RUBISCO hydrolysis was found in the last cm of the gel segment but no polypeptide band was detected after SDS-PAGE. It seems that more than one major gelatin/RUBISCO-digesting proteinase may occur in nematode extracts.

Gelatin-Affinity Chromatography

Fractions which were eluted from the gelatin-agarose column digested RUBISCO and possessed a protein with a Mr of 62K. 30 µg of female protein loaded onto the gelatin-agarose column was sufficient to detect the M62K protein by silver staining.

6) The Use of a Mercuryl Column to Isolate G. pallida Proteinases

Figure 7:
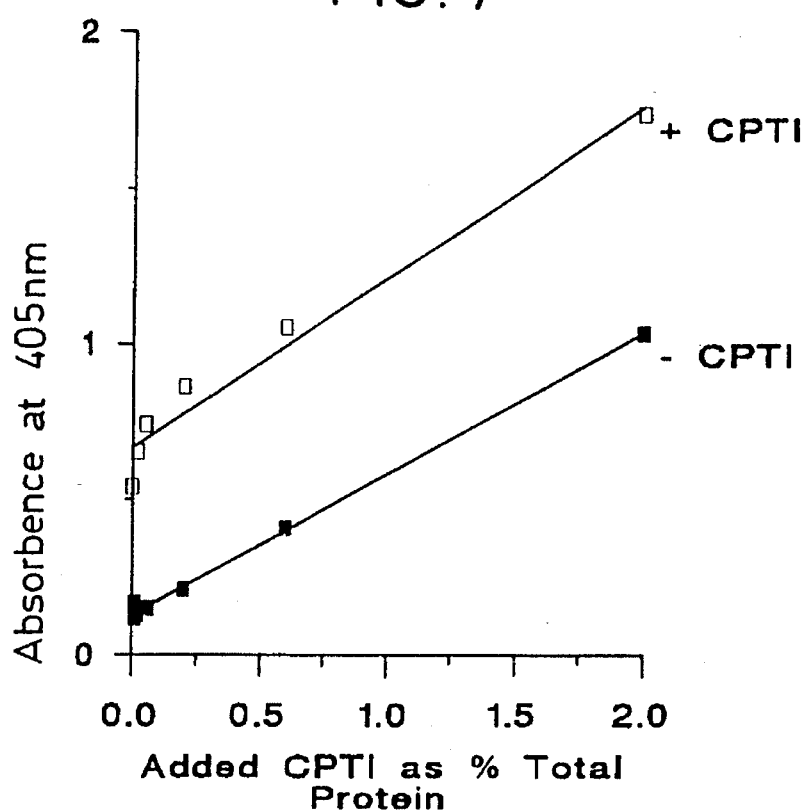
FIG. 7 refers to Example 4 and shows that the level of expression of CpTi in CpTi-expressing plants is about 1% of total protein.

Proteins liberated from the PAMBA-agarose column exhibited proteolytic activity in a gelatin-acrylamide gel, but to a lesser extent than proteinases obtained directly from crude extracts (FIG. 7). Silver staining revealed a PAMBA-agarose immobilised protein with an Mr value of 62K. This work supports the previous finding which suggested that this is the Mr of the major proteinase found in female nematode and that it is probably a cysteine-type proteinase.

Example 4

Effect of Low Levels of Expression of CpTi
Raising a polyclonal antibody against CpTi.

Two female Balbc mice of five weeks received an intraperitoneal injection of 10 µg CpTi in 50:50 Freund's complete adjuvant and distilled water. After three weeks both received a further similar injection using Freund's incomplete adjuvant. After preliminary testing of antibody titre, one mouse was sacrificed three weeks after its last injection and its serum used at 1:2500 dilution for detecting CpTi in roots. A standard enzyme linked immunosorbent assay (ELISA) was used. Roots were ground on ice using a mortar and pestle in PBS (phosphate buffered saline; pH 7) plus insoluble polyvinyl pyrrolidone. The material was then homogenized before being spun at 10000 g for 2 min and the supernatant collected. Microtitre plates (NUNC) were coated for >48 h at 4° C. with 5 µg root protein/ml of carbonate buffer at pH 9.6. Both CpTi and non-CpTi expressing plants were treated similarly and a set of internal standards was used by adding 0–60 ng added CpTi/5 µg root protein. Plates were washed with PBS and blocked using 1% Bovine Serum Albumin (BSA:Sigma) in PBS-tween. After further washing in PBS-tween, the anti-CpTi antibody was added at 1:2500 in PBS-tween plus 0.1% BSA for 2 h, the plates washed 8 times in PBS-tween before the second antibody of an anti-mouse IgG antibody conjugated to alkaline phosphatase was added at the concentration recommended by the supplier (Sigma: product A5153) for 2 h in 0.1% BSA plus 1% goat serum. The plates were re-washed as before and the substrate p-nitrophenyl phosphate added at 1 mg/ml buffer at pH 9.8 (10% diethanolamine and 0.5 mM $MgCl_2$). Readings were measured about 24 h later at 405 nm using a standard plate reader (Biorad). An example set of results is shown for roots of plants sampled concurrently with the data shown in FIGS. 3–6. One regression line is for CpTi expressing plants (+CpTi) and the other for plants not expressing CpTi (–CpTi). In both cases 0–60 ng CpTi have been added to sub-samples of the prepared homogenates. The difference between the two regression lines in FIG. 7 establishes the level of expression in the CpTi expressing plants to be about 1% total protein.

Effect of low levels of expression of CpTi on G. pallida.

CpTi expressing plants shown by ELISA to be expressing 0.1–0.5% total soluble protein as CpTi were used to confirm the influence of CpTi on development of G. pallida and to determine if levels of about 1% were necessary to achieve a substantial effect on this nematode. Experiments were conducted with plants in pouches as described earlier with 50J2 added per selected root tip.

The results establish that plants expressing low levels of CpTi (0.1–0.5%) had a significantly lower ratio of nematodes that could be sexed as female rather than male compared to two types of control plant (Table 4). This difference could not be attributed to a delay in development to the point at which sex can be determined (Table 5).

TABLE 4

The values are the number of immature males and females observed on roots of the potato plants at 12–19 days post-invasion. Untransformed plants were cv Desiree and the CpTi negative plants and CpTi positive plants are similar to those described earlier except the CpTi positive plants showed only 0.1–0.5% CpTi expression. The density of animals on these plants were 4–12 nematode/infected root tip with a controlled infection of up to a maximum of 4 root tips per plant. Data was collected from more CpTi expressing plants than the controls.

|  | Root tips Examined | Nematodes/ Males | Root Tip Females |
|---|---|---|---|
| CpTi negative | 25 | 3.56 ± 0.29 | 2.36 ± 0.42 |
| CpTi positive* | 94 | 4.64 ± 0.06 | 1.71 ± 0.03 |

*The male:female ratio is greater for CpTi positive than CpTi negative plant lines ($X^2 = 17.4$; $P < 0.005$).

TABLE 5 cv Desiree and CpTi plants were harvested at 12 days post infection and the ratio of immature individuals divided into those that could or could not be sexed at that time.

|  | Numbers | | % | |
|---|---|---|---|---|
| Test Plant | unsexed | sexed juveniles | unsexed | sexed |
| Desiree | 74 | 57 | 56 | 44 |
| CpTi positive | 158 | 107 | 60 | 40 |

There is no significant difference in the proportion of nematodes that could be sexed on the two types of plant ($X^2 = 0.35$; NS).

The effect of low levels of CpTi expression on *Meloidogyne incognita*.

Both CpTi expressing and non-expressing potato plants were transplanted from tissue culture to a sandy loam for 4 weeks to allow their establishment in soil. They were then transplanted to soil in which tomatoes heavily infected with *Meloidogyne incognita* had been grown. The plants were grown in a controlled environment chamber at 25° C. for 36 days and the roots harvested. The majority of each root system was collected for egg counts using four plants expressing CpTi and five plants not expressing this gene. The eggs were removed from each root sample using 1% sodium hypochlorite for 2 min and the egg numbers recovered from each plant were counted using a standard counting slide. The proportion having embryonated to a formed juvenile were assessed for 100 eggs chosen at random. A minor part of each root system was bulked for the two plant lines to carry out the ELISA to detect CpTi as outlined earlier.

The results from ELISA suggest that the level of expression of CpTi was only 0.1–0.2% total soluble protein. In spite of this low level of expression, the CpTi positive plants did have an effect on *M. incognita*. The number of eggs laid by the females at 36 days is significantly less for the CpTi expressing than the control plants ($P<0.0005$; Table 6). The percentage embryonation of females parasitizing the two lines of plants was very similar (Table 6). If CpTi had delayed the maturing of females then more unembryonated eggs would be expected than in the controls. However, the results suggest that the main effect is in reducing the daily egg laying rate which would not be expected to influence the proportion of laid eggs that had embryonated once at the gall surface.

TABLE 6

Number of eggs associated with galls caused by females of *Maloidogyne incognita* on potato 36 days at 25° C. after transfer of these plants to infested soil.

| Test Plant | Eggs/g root | % embryonation to juvenile |
|---|---|---|
| CpTi negative | 5702 ± 1397 | 37.5 |
| CpTi positive* | 1388 ± 406 | 41.5 |

*The difference in number of eggs/g root is statistically significant. The means above were obtained using transformed values ($\log_{10}$) but are shown as arithmetic values after back transformation; $t < 0.005$ based on analysis of logarithmically transformed data.

The significance of the data shown in this example is as follows:

a) The raising of the antibody allows the level of CpTi expression in the roots to be measured. It confirms the presence of CpTi in test plants.

b) The clear effect obtained in the data on sex ratios was obtained with plants showing expression of 1%.

c) The experiments with lower levels of CpTi expression confirm the original effect on sex ratio suggesting that CpTi is effective in the period after the animal begins to feed but before sexual differentiation of the animals. This is consistent with the results in the first filing which suggest CpTi has an effect against the J2 and J3 stages which are the first two stages to feed in the plate. This early effect of CpTi is not due to slowing rate of development (Table 7).

d) The results with *Meloidogyne incognita* are interesting. In this nematode (a root-knot nematode), the female feeds from giant cells she induces in host roots and the plant also responds by forming a gall (knot) around each female or small group of females. The eggs are laid individually at the rate of several per day onto the gall through a lesion between the vulva of the female to the gall surface. Eggs embryonated in a gelatinous matrix that is exuded by the female around them (the hypochlorite used is the standard way of removing eggs from their matrix). The fact that the embryonation of CpTi+ and CpTi− is similar suggests that the eggs were laid over the same time period. Therefore the difference in Table 6 is due to dissimilar rates of laying and not in the time taken for the animal to develop to the point at which the females begin to lay eggs.

Example 5

Rice- and Maize-derived Proteinase Inhibitors also show Activity in vitro

Preparation of proteinase inhibitors from rice.

The extraction procedures followed those given by Abe, K. Kondo, H & Arai, S. (1987 Agric. Biol. Chem. 51 2763–2768) to isolate oryzacystatin (see below). 50 g of brown rice meal was extracted for 1 h in 130 ml of 25 mM phosphate buffer pH 7 containing 0.15M NaCl. The supernatant was collected by centrifugation at 7000 g at 4° C. for 20 min. The clear supernalant was heated at 80° C. for 10 min.

The mixture was centrifuged again as above and 30% ammonium sulphate was added to the supernatant for 1 h on ice. The precipitate was removed by centrifugation before further ammonium sulphate was added to 65% saturation. The precipitate was collected after centrifugation, resuspended in 10 ml of 50 mM acetate buffer (pH 4.9) and dialyzed overnight against the same buffer at 4° C. The solution was passed through a CM SEPHADEX® C50 column (1.5×24cm) which had been pre-equilibrated with acetate buffer (pH 4.9). Proteins were eluted in a 0–0.4M NaCl linear gradient and those fractions showing an ability to inhibit papain in the microtitre plate assay described below were collected. The fractions with inhibitory activity were pooled to form rice preparation 1 (Table 7). An aliquot was dialyzed against 50 mM phosphate buffer (pH 6) containing 2 mM EDTA and 2 mM cysteine before loading onto a papain agarose column equilibrated with the same buffer but also containing 0.1% Brij 35. Proteins eluted with 50 mM $K_3PO_4$ (pH 11.50) in 0.5M NaCl. The elutant was brought to pH 6.5 with 3M sodium formate buffer (pH 2.9) and dialyzed against $dH_2O$ before use as rice prepaxation II.

Preparation of inhibitors from maize meal 40 g of maize meal was mixed overnight in 250 ml 25 mM phosphate buffer (pH 7.1) containing 0.1M NaCl at 4° C. and filtered through Whatman No1 filter paper. The flitrate was spun at 20000 g for 30 min at 4° C. and the clear supernatant brought to 25–85% ammonium sulphate saturation. The pellet obtained by centrifugation at 20000 g for 10 min at 4° C. was redissolved in water and dialyzed overnight at 4° C. before use as the preparation containing inhibitors from maize.

Proteolytic activity of G. pallida

Freshly hatched juveniles of G. pallida were incubated in 2.5 mM 5'hydroxytryptamine in water at 20° C. for 4 h. This caused material to exude from the mouth which can be visualized at the mouth by allowing the protein stain Ponceau S to diffuse through a small aliquot of the experimental sample containing the nematodes under a microscope slide and coverslip. Worms were removed from the medium by centrifugation at 3000 g for 2 min before the fluid was dialyzed at 4° C. against distilled water overnight. The material was freeze-dried in aliquots at −70° C. until use and reconstituted to 2.5 μg protein/ml $dH_2O$ at 5° C. immediately before use. Assays were carried out in a reaction mixture prepared by mixing 50 μl of this solution with 20 μl of either 100 mM phosphate buffer at pH 6.8 or 100 mM titrate/phosphate buffer at pH 5 plus either 10 μl of the inhibitor under test at the concentrations given in Table 7 or $dH_2O$ for corresponding control rates for the uninhibited exudate.

The assays were carried out by coating microtitre plates (NUNC) with 50 μl of 0.01 μg/ml biotin/gelatin in carbonate buffer (pH 9.6) overnight at 4° C. The plates were blocked with 1% gelatin and washed with PBS before adding 75 μl of freshly prepared reaction mixture for 18 h. The reaction was stopped by washing wells eight times with PBS-tween before adding 100 μl of avidin-conjugated alkaline phosphatase with 1% goat serum to each well for 1 h. The wells were washed as before with PBS-tween followed by 2 rinses in PBS before addition of 100 μl of 1 mg/ml P-nitrophenyl phosphate in substrate buffer (10% diethanolamine and 0.5 mM $MgCl_2$) at pH 9.8. The color development was read at 405 nm using a plate reader (Biorad). All samples were compared against a reference blank which lacked nematode exudate preparation in the reaction mixture.

TABLE 7

The effect of various inhibitors of proteolytic activity of the 5HT-induced exudate from J2. Values are percentages based on the difference between values for the uninhibited exudate sample and the corresponding control lacking added exudate sample.

| Inhibitor/activator | Relative Activity (% of controls at that pH) | |
| --- | --- | --- |
| | pH 5 | pH 6.8 |
| Control (no inhibitor) | 100 | 100 |
| CpTi at 10 μg/ml | 39* | 91 |
| Rice preparation I (30 μg/ml) | 84* | 83* |
| Rice preparation II (30 μg/ml) | 100 | 70* |
| Cysteine | >100 | 100 |
| EDTA | >100 | 93 |
| E64 | 0 | 5* |
| Maize preparation (20 μg/ml) | — | 9* |

—, not tested.
*significantly different from control values (P < 0.05; ANOVA, LSD = 10.9%)

The results establish mat the proteolytic activity of the exudate shows a different pattern of inhibition at the two pH values. That at pH 5 shows cysteine proteinase activity in that it is inhibited by E64 and is stimulated by the two known activators of cysteine proteinases (cysteine and EDTA). Both CpTi and the rice preparation I inhibit this activity.

The proteolytic activity at pH 6.8 was not inhibited by CpTi or stimulated by cysteine as expected of a cysteine proteinase. However both rice preparations showed some inhibitory effect against this proteolytic activity which was also inhibited by EDTA. The preparation from maize was a very effective inhibitor of this proteolytic activity.

Figure 8:
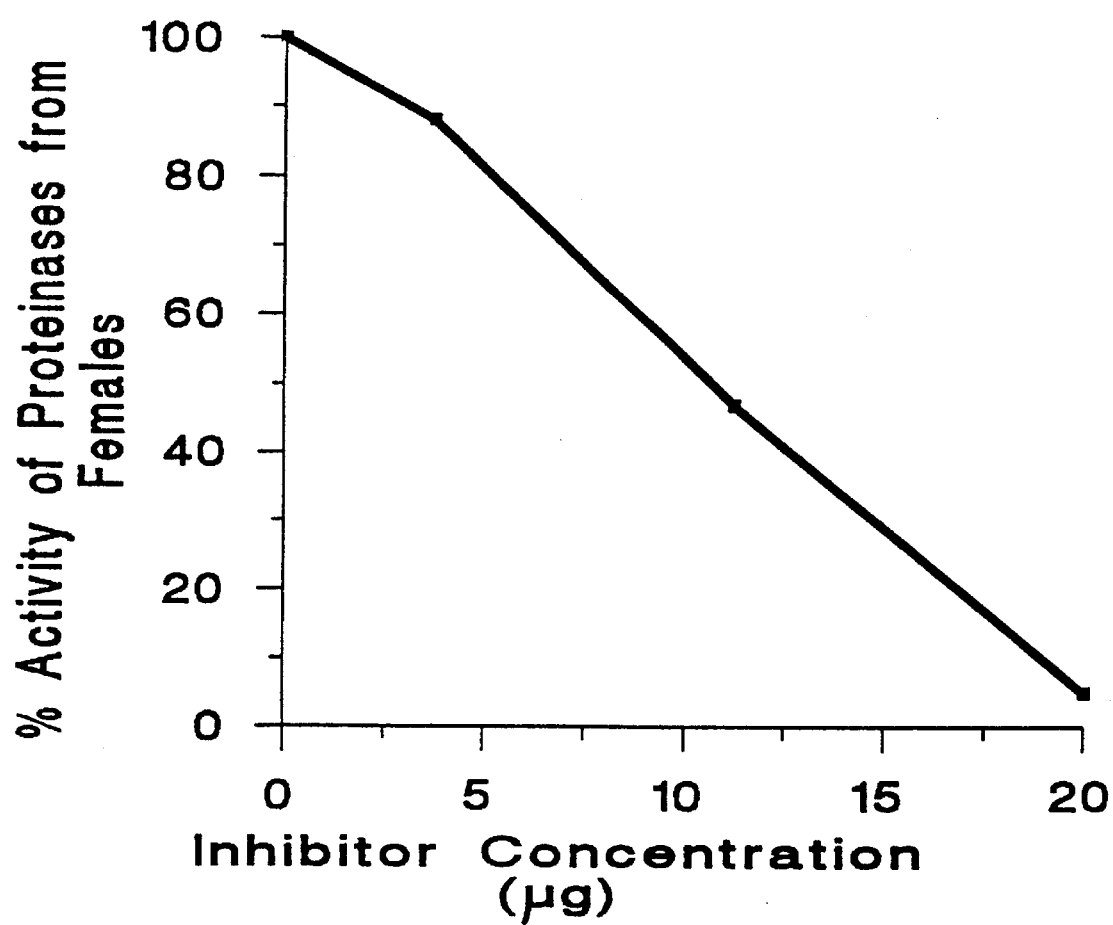
FIG. 8 refers to Example 5 and shows the inhibitory effect of different concentrations of maize-derived proteinase inhibitor.

Further studies were based on the same assay but using whole homogenates of female G. pallida as the source of proteinase activity. The results confirmed the two optima for proteolytic activity at pH 5.7 and pH 6.8 already obtained by other methods. The most effective inhibitor under the conditions of the experiment was the protein preparation from maize meal. Therefore this was investigated further by varying the total protein concentration of the preparation from maize over the range 0–2 μg in the microtitre plate assay which was otherwise conducted as before. This showed that 50% inhibition occurred at about 10 μg protein of the inhibitor preparation with virtually no activity remaining at 20 μg/ml (FIG. 8). Passage of the preparation through a papain affinity column (Sigma) did not prevent inhibition in the plate assay suggesting the presence of an inhibitor which is not of the subgroup of cysteine proteinases with particular activity against papain.

The significance of the data shown in this example is as follows:
a) The exudate is principally (but not necessarily exclusively) made up of secretions that the animal puts into plants.
b) The use of exudate for J2 is therefore good evidence for inhibition not just of proteinases possessed by the animal but more specifically those secreted into the plant.
c) The data shows the efficacy of CpTi at pH 5 rather than pH 6.8 against J2. The proteinase at pH 5 has cysteine-like activity.
d) It shows some efficacy for the rice preparations containing oryzacystatin.
e) It emphasizes the high efficacy of the inhibitor from maize at pH 6.8. This is also shown by FIG. 8.

EXAMPLE 6

Isolation of a Gene for Another Cysteine Proteinase Inhibitor (Oryzacystatin)

The results for CpTi establish an effect in transgenic plants on both *Globodera pallida* and *Meloidogyne incognita* and also for proteinases in both homogenates of females of *G. pallida* and exudates from its juveniles. CpTi has been reported to have its principal activity as a serine proteinase inhibitor whereas the data presented earlier (Table 3 and 7) establish that *G. pallida* also possesses cysteine proteinases.

This indicates a rational approach to the design of resistance against nematodes involves four stages:

(i) Define the proteinases present in the animals using approaches such as those given in this application (ii) Isolate proteinase inhibitors and identify those with activity against such proteinases (iii) Isolate the gene(s) for the inhibitor(s) of interest (iv) Transform the crop plant with a cassette including the gene(s) of interest (an example is given earlier).

As an example, stage one has been established for *Globodera pallida* and inhibitors of interest such as CpTi, and the cysteine inhibitors from maize and rice have been shown to inhibit the proteinases of the nematode. Procedures such as those given above to obtain inhibitors from maize and rice could also be used to isolate other proteinase inhibitors. The isolated protein or peptide fragments obtained by digestion by proteinases such as endoproteinase Glu-C from *Staphylococcus aureus* V8 (Sigma) can be used to gain peptide sequence information using standard procedures that are even available as a commercial service. This information can be used to design a group of redundant oligonucleotide primers for use in experiments to isolate the gene. The procedures are commonly carried out and were used by to design oligonucleotide probes to screen a cDNA library for rice to obtain the cysteine inhibitor oryzacystatin from rice (Abe, Emori, Kondo, Suzuki and Arai, 1987, *J. Biological Chemistry* 262 16793–16797). As an example of Stage III, exact rather than redundant oligonucleotides have been synthesized since the sequence of oryzacystatin I is known from sequencing of genomic clone (Kondo, Emori, Abe, Suzuki & Arai, 1989, Gene 81 259–265). This gene has an intron in the middle of its coding sequence. Therefore primers were designed to DNA sequence at the 5' and 3' ends of both exon 1 and 2. The design (see Table 8) accommodated a SmaI site and NdeI in primer 1 at 5' to the start codon and an EcoRI site at 3' to the coding region of exon 2 (primer 4).

*Oryza sariva L. japonicum* was grown until the tillers were about 10 cm high and these were harvested to liquid nitrogen in approximately 1 g aliquots. Genomic DNA was extracted from this material using the standard method described by Dellaporta, Wood & Hicks (1984, A Maize DNA Miniprep p36–37 In: Maimberg, Messing, Sussex (ed) Molecular Biology of Plants: A Laboratory Course Manual, Cold spring Harbor Press, Cold Spring Harbor, N.Y., USA).

Oryzacystatin I was amplified from the genomic DNA using the polymerase chain reaction (PCR) (for procedures see McPherson, Oliver & Gurr, 1991, In: McPherson, Quirke & Taylor (ed), PCR: *A Practical Approach*, IRL at Oxford University Press, Oxford, UK). This involved aliquots to one tube: 5 µl5×PCR buffer (Northumbria Biologicals), 5 µl of a 2 mM dNTP soln. (Pharmacia) 10 pMoles of each primer (primers 1 and 4 in Table 8), 0.1–0.5 µg target DNA in 1 µl and sufficient $dH_2O$ to make a volume of 50 µl after adding 2.5 units of Taq polymerase (Northumbria Biologicals). The reaction mix was overlaid with 50 µl mineral oil before beginning PCR. This was carried out using a temperature cycier (LEP) with the conditions of 5 min at 95° C. followed by 40 cycles of 95° C. for 1 min, 55° C. for 1 min and 72° C. for 2 min. The samples were then cooled to 4° C. until collection.

The PCR products were subjected to electrophoresis using low melting point agarose and a DNA band of the expected length (about 650 bp) was visualized using ethidium bromide (see Sambrook, Fittsch & Manjarls, (1989) Molecular Cloning: *A Laboratory Manual* 2nd edition 3 vols, Cold spring Harbor Press, Cold Spring Harbor, N.Y., USA for this and other techniques for DNA manipulation used in this work).

The DNA of interest was recovered from the gel by excising the band and placing it in a Spin-X tube (Costar). The tubes were cooled to −20° C. for 20 min, spun in a microfuge for 5 min and the last two steps repeated before collecting the DNA in about 500 µl of solution. The DNA was recovered by ethanol precipitation (Sambrook et al 1989 supra).

This DNA sample was used in PCR as described above but using (i) primers 1 and 2 and (ii) primers 3 and 4 to achieve amplification of exons 1 and 2 respectively with the additional bases added with the primers (Table 8). These products were then recovered as already described.

The identity of the original amplified DNA and the subsequent exon 1 and exon 2 was was confirmed using three restriction enzymes. For exon 1; 1 µg DNA, 2 µl of one for all buffer (Pharmacia), 5 µl $dH_2O$ buffer and 5 units SalI. For exon 2 as for exon 1 but either 5 units SacI or 5 units HindIII. Controls were run for both exons without restriction enzymes. In both cases the DNA was cut at the expected positions from the known restriction sites (Kondo, Emori, Abe, Suzuki and Arai. 1989, supra). Exon 1 and exon 2 were joined using the PCR approach of recombination by overlap extension (Horton & Pease 1991, In: Directed Mutagenesis: *A Practical Approach*; Ed McPherson M. J. IRL Press at Oxford University hess, Oxford UK). Primers 1 and 4 were used with conditions as above except the temperature cycling was; 94° C. for 2 min, 94° C. 30s, 58° C. 2 min and 72° C. for 1 min. The PCR reaction products were separated by electrophoresis using 1% low melting point agarose. The major band (about 300 bp) was excised from the gel and the DNA recovered as described above. The DNA was digested using EcoRI and SmaI as described earlier and the reaction stopped by heat inactivation. The digestion products were ligated into prepared pBluescript II KS+ and SK+ (Strategene). The ligation mix was used to transform competent *E. coli* DM5-α. Recombinants were selected by insertional inactivation of β-galactosidase (Blue/white screening) and picked into LB.amp media. Subsequent plasmid preparations from these clones gave 300 bp inserts when digested with EcoRI and SmaI. Sequencing this insert has confirmed that it consists of exon 1 joined at its 3' end to exon 2 joined without addition or loss to the coding sequence. These standard procedures were carried out using protocols provided by the supplier and a standard practical text (Sambrook et al 1989 supra). PCR is very dependent on the particular characteristics of the thermal cycler and chemicals used. Therefore it may be necessary to adjust the conditions given above for each PCR reaction to optimise the production of reacton products.

This isolated DNA is now suitable for use in a cassette for plant transformation as described elsewhere in this patent application.

The significance of the data shown in this example is as follows:

a) Once the invention was made it seemed likely that other proteinase inhibitors may be at least as effective as CpTi. There are probably differences in proteinases present between nematode species and also between life-stages of a species. Both oryzacystatin I and II have been described.
b) Cysteine proteinase inhibitors seem of particular interest. By means of the invention, it is possible to take a nematode, determine which inhibitors are effective against it, and isolate the gene for use in a cassette for transgenesis purposes.
c) Oryzacystatin I and II are vailable as cDNA clones.

TABLE 8

Primer design used to isolate exon 1 and exon 2 and then to recombine them without the intron using overlap extension.

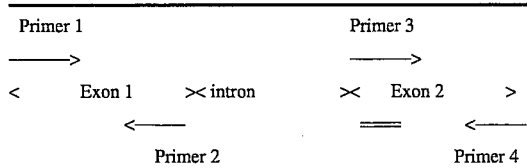

=== is the extension on primer 2 complementary to 5' of exon 2 and primer 3 for recombination by overlap extension.

Exon 1 has a SalI site: Exon 2 has HindIII and SacI sites

Primer 1: Coding strand (SEQ ID NO: 1)

[——— EXON 1 ———>
5'> GGAGAAGGCCCGGGGCAT AT GT CGAGCGACGGAGGGCC <3'
         ———————     ———————
         Sma I       Nde I

Primer 4: Non-coding strand (SEQ ID NO: 2)
         [—— exon 2 on
              coding    strand    ——>
5'> ACATGTAGAATTCTTAGGCATTTGCACTGGC < 3'
         ———————
         Eco RI Primer 2: Non-coding strand (SEQ ID NO: 3)
<—— exon 2 on
     coding    strand    ———]
5'> CTCGAACTCTAGAAGAGAATTGGCCTTCTTGTTGTG <3'
         ———————
         Xba I Primer 3: Coding strand (SEQ ID NO: 4)
[—— Exon 2 ————>
5'>AATTCTCTTCTAGAGTTCGAG <3'
    ———————
    Xba I

What is claimed is:

1. A method of controlling nematodes comprising providing a proteinase inhibitor in an effective amount to a plant sufficient to control nematodes.

2. A method of controlling nematodes comprising providing a proteinase inhibitor in an effective amount to a locus sufficient to control nematodes in plants.

3. A method of conferring nematode resistance on a plant, comprising modifying or transforming said plant to express a gene or other DNA coding for a proteinase inhibitor and selecting said modified or transformed plant which expresses said proteinase inhibitor such that said modified or transformed plant exhibits nematode resistance.

4. The method as claimed in any one of claims 1 to 3, wherein said proteinase inhibitor belongs to the Bowman-Birk family.

5. The method of claim 4, wherein said proteinase inhibitor is cowpea trypsin inhibitor (CpTi).

6. The method of claim 5, wherein said CpTi is encoded by a DNA sequence which hybridizes under stringent conditions to a DNA sequence encoding a trypsin inhibitor isolatable from cowpea.

7. The method of claim 6, wherein said CpTi is iso-inhibitor fIV.

8. A method as claimed in any one of claims 1 to 3, wherein said nematode is of the genus Heterodera or Globodera.

9. The method of claim 8, wherein said nematode is *H. glycines, H. shachrii*(beet cyst nematode), *H. avenae* (cereal cyst nematode), *G. rostochiensis* or *G. pallida* (potato cyst nematode).

10. The method as claimed in any one of claims 1 to 3, wherein said nematode is of the genus Meloidogyne.

11. The method of claim 10, wherein said nematode is of the species *M. javanica, M. hapla, M. arenaria* or *M. incognita.*

12. A method as claimed in any one of claims 1 to 3, wherein said plant is tobacco, cotton, or oilseed rape.

13. A method as claimed in any one of claims 1 to 3, wherein said plant is an ornamental plant.

14. A method as claimed in any one of claims 1 to 3, wherein said plant is a crop selected from soybean, sugar beet, tomato, or potato.

15. A method as claimed in any one of claims 1 to 3, wherein said plant is a cereal plant.

16. A method of conferring nematode resistance on a plant, comprising modifying or transforming said plant to express a gene or other DNA coding for a Bowman-Birk family proteinase inhibitor and selecting said modified or transformed plants which express said proteinase inhibitor such that said modified or transformed plants exhibit nematode resistance.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

GGAGAAGGCC CGGGGCATAT GTCGAGCGAC GGAGGGCC  38

( 2 ) INFORMATION FOR SEQ ID NO:2:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

ACATGTAGAA TTCTTAGGCA TTTGCACTGG C  31

( 2 ) INFORMATION FOR SEQ ID NO:3:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

CTCGAACTCT AGAAGAGAAT TGGCCTTCTT GTTGTG  36

( 2 ) INFORMATION FOR SEQ ID NO:4:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

AATTCTCTTC TAGAGTTCGA G  21